US009511141B2

(12) United States Patent
Kawaguchi

(10) Patent No.: US 9,511,141 B2
(45) Date of Patent: Dec. 6, 2016

(54) COMPOSITION FOR REDUCING OXIDATIVE STRESS AND/OR SIDE EFFECTS OCCURRING DURING CANCER CHEMOTHERAPY OR IMPROVING NUTRITIONAL STATUS DURING CANCER CHEMOTHERAPY

(75) Inventor: Susumu Kawaguchi, Meguro-ku (JP)

(73) Assignee: NUTRI CO., LTD., Yokkaichi-Shi, Mie (JP)

( * ) Notice: Subject to any disclaimer, the term of this patent is extended or adjusted under 35 U.S.C. 154(b) by 44 days.

(21) Appl. No.: 12/811,682

(22) PCT Filed: Jan. 6, 2009

(86) PCT No.: PCT/JP2009/050020
§ 371 (c)(1),
(2), (4) Date: Jul. 2, 2010

(87) PCT Pub. No.: WO2009/087988
PCT Pub. Date: Jul. 16, 2009

(65) Prior Publication Data
US 2010/0291057 A1    Nov. 18, 2010

(30) Foreign Application Priority Data
Jan. 9, 2008   (JP) ................................. 2008-001801

(51) Int. Cl.
| A61K 45/06 | (2006.01) |
| A61K 31/015 | (2006.01) |
| A61K 31/07 | (2006.01) |
| A61K 31/122 | (2006.01) |
| A61K 31/191 | (2006.01) |
| A61K 31/355 | (2006.01) |
| A61K 31/375 | (2006.01) |
| A61K 31/4415 | (2006.01) |
| A61K 31/455 | (2006.01) |
| A61K 31/51 | (2006.01) |
| A61K 31/525 | (2006.01) |
| A61K 31/593 | (2006.01) |
| A61K 31/714 | (2006.01) |
| A61K 33/24 | (2006.01) |
| A61K 33/30 | (2006.01) |

(52) U.S. Cl.
CPC ............ *A61K 45/06* (2013.01); *A61K 31/015* (2013.01); *A61K 31/07* (2013.01); *A61K 31/122* (2013.01); *A61K 31/191* (2013.01); *A61K 31/355* (2013.01); *A61K 31/375* (2013.01); *A61K 31/4415* (2013.01); *A61K 31/455* (2013.01); *A61K 31/51* (2013.01); *A61K 31/525* (2013.01); *A61K 31/593* (2013.01); *A61K 31/714* (2013.01); *A61K 33/24* (2013.01); *A61K 33/30* (2013.01)

(58) Field of Classification Search
CPC .................................................... A61K 45/06
See application file for complete search history.

(56) References Cited

U.S. PATENT DOCUMENTS

| 6,077,828 | A | 6/2000 | Abbruzzese et al. | |
| 6,326,355 | B1 | 12/2001 | Abbruzzese et al. | |
| 6,361,800 | B1 | 3/2002 | Cooper et al. | |
| 6,387,883 | B1 | 5/2002 | Abbruzzese et al. | |
| 7,223,736 | B2 | 5/2007 | Abbruzzese et al. | |
| 2002/0068102 | A1* | 6/2002 | Su et al. | 424/765 |
| 2002/0099020 | A1 | 7/2002 | Abbruzzese et al. | |
| 2002/0146463 | A1 | 10/2002 | Clayton | 424/617 |
| 2005/0008690 | A1 | 1/2005 | Miller | |
| 2005/0142124 | A1* | 6/2005 | Kaiser | 424/94.1 |
| 2006/0182729 | A1* | 8/2006 | Prasad et al. | 424/94.1 |
| 2007/0098762 | A1* | 5/2007 | Stahl et al. | 424/439 |
| 2007/0116802 | A1* | 5/2007 | Germano | 426/72 |
| 2007/0196445 | A1 | 8/2007 | Abbruzzese et al. | |
| 2010/0150894 | A1 | 6/2010 | Wakabayashi et al. | |

FOREIGN PATENT DOCUMENTS

| EP | 0 564 804 | 2/1993 |
| EP | 0564804 | 10/1993 |
| EP | 0564804 A1 | 10/1993 |
| JP | H6-48954 A | 2/1994 |
| JP | 11-508282 A | 7/1999 |
| JP | 2002-335913 | 11/2002 |
| JP | 2004-515508 A | 5/2004 |
| WO | 02-47493 | 12/2001 |
| WO | WO0247493 | 6/2002 |
| WO | WO 2006108008 A2 * | 10/2006 |
| WO | 2006/117405 A1 | 11/2006 |
| WO | WO2006117405 | 11/2006 |
| WO | 2007/013556 A1 | 2/2007 |

OTHER PUBLICATIONS

Opara, "Oxidative Stress, Micronutrients, Diabetes Mellitus and its Complications," The Journal of the Royal Society for the Promotion of Health, vol. 122, No. 1, pp. 28-34 (2002).*

(Continued)

*Primary Examiner* — Dennis J Parad
(74) *Attorney, Agent, or Firm* — Morgan, Lewis & Bockius LLP

(57) ABSTRACT

Provided is a composition for reducing oxidative stress and/or side effects occurring during cancer chemotherapy or improving a nutritional status during cancer chemotherapy. The composition is one for reducing oxidative stress and/or side effects occurring during cancer chemotherapy or improving nutritional status during cancer chemotherapy and comprises the following components (a) to (f): (a) an antioxidant agent; (b) at least one component selected from the group consisting of vitamin $B_1$, vitamin $B_2$, vitamin $B_6$, niacin, and pantothenic acid; (c) at least one component selected from the group consisting of folic acid, vitamin $B_{12}$, and vitamin A; (d) zinc; (e) selenium; and (f) coenzyme Q10.

14 Claims, 23 Drawing Sheets

(56) References Cited

OTHER PUBLICATIONS

Ladas et al, "Antioxidants and Cancer Therapy: A Systematic Review," Journal of Clinical Oncology, vol. 22, No. 3, pp. 517-528 (2004).*
Pravst et al, "Coenzyme Q10 Contents in Foods and Fortification Strategies," Critical Reviews in Food Science and Nutrition, vol. 50, Issue 4, pp. 269-280 (2010).*
Drisko, MD et al., "The Use of Antioxidants with First-Line Chemotherapy in Two Cases of Ovarian Cancer" Journal of the American College of Nutrition, vol. 22, No. 2, pp. 118-123, 2003.
Jatoi et al., "Is voluntary vitamin and mineral supplementation associated with better outcome in non-small cell lung cancer patients? Results from the Mayo Clinic lung cancer cohort" Lung Cancer, vol. 49, pp. 77-84, 2005.
Lockwood et al., "Apparent Partial Remission of Breast Cancer in 'High Risk' Patients Supplemented with Nutritional Antioxidants, Essential Fatty Acids and Coenzyme Q10" Molec. Aspects Med. vol. 15 (Supplement), pp. s231-s240, 1994.
Extended European Search Report mailed Apr. 29, 2013 for International Application No. PCT/JP2009/050020 (5 pages).
Office Action issued in Japanese Patent Application No. 2009-548912 mailed Jul. 16, 2013.
Office Action issued in Japanese Patent Application No. 2009-548912 mailed Oct. 8, 2013.
Office Action issued in Japanese Patent Application No. 2009-548912 mailed Mar. 31, 2015.
Office Action issued in Japanese Patent Application No. 2009-548912 mailed Jun. 30, 2015.
Nutrition management for cancer patients care for cancer cachexia—, p. 172-176 and p. 254-258, editorial supervisor Ichiro Urushizaki, Medical Review Co. Ltd., issued on May 30, 1994 (partial translation).
Nursing, vol. 46, No. 6, p. 199-p. 212 (1994) (partial translation).
Ladas et al., "Antioxidants and cancer therapy: A systematic review," Journal of Clinical Oncology, 22(3):517-528 (2004).

* cited by examiner

COMPOSITION FOR REDUCING OXIDATIVE STRESS AND/OR SIDE EFFECTS OCCURRING DURING CANCER CHEMOTHERAPY OR IMPROVING NUTRITIONAL STATUS DURING CANCER CHEMOTHERAPY

CROSS REFERENCE TO RELATED APPLICATION

This application is a national stage of international application No. PCT/JP2009/050020 filed on Jan. 6, 2009, which also claims priority under 35 USC 119 to Japanese Patent Application No. 2008-001801 filed Jan. 9, 2008, the entire content of which are incorporated herein by reference.

TECHNICAL FIELD

The present invention relates to a composition for reducing oxidative stress and/or side effects occurring during cancer chemotherapy or improving a nutritional status during cancer chemotherapy.

BACKGROUND ART

During application of cancer chemotherapy, the bone marrow, the nerve tissues, the gastrointestinal mucosal cells, and the like are damaged due not only to the underlying disease but also to an influence of an adverse effect of the drug, and side effects such as bone marrow suppression, renal disorder, nausea, vomiting (anorexia), alopecia, and stomatitis develop (Non-Patent Document 1).

During application of cancer chemotherapy, because active oxygen attributable to a biological damage caused by the chemotherapy is produced in abundance, consumption of an antioxidant substance that captures the active oxygen thus produced is increased.

Also, while the required amount of zinc is increased to accommodate enhanced DNA synthesis and protein synthesis for repair of damaged tissues, the amount of urinary excretion of zinc is increased due to inflammation. Accordingly, it is important to supplement sufficient amounts of trace nutrients such as antioxidant vitamins and zinc.

However, because main side effects of cancer chemotherapy are anorexia, stomatitis, and vomiting, sufficient intake amounts cannot be secured, and therefore supplementation of trace nutrients cannot rely on a dietary source alone. Further, deficiency in trace nutrients such as zinc aggravates taste and olfaction disorder and delay in wound healing, with the potential risk for creating a vicious circle. It is important to implement a preventive measure against these side effects from the viewpoint of quality of life (QOL) as well.

Non-Patent Document 1: ITO, Akihiko, Japan J. Cancer Chemother 29(4), 2002

DISCLOSURE OF THE INVENTION

Problem to be Solved by the Invention

An object of the present invention is to provide a composition for reducing oxidative stress and/or side effects occurring during cancer chemotherapy or improving a nutritional status during cancer chemotherapy.

Means for Solving the Problem

The present inventors asked candidate patients for cancer chemotherapy to take a composition containing the following components (a) to (f) in order to verify the usefulness of the composition. As a result, they have found that the composition is effective in reducing oxidative stress and/or side effects occurring during cancer chemotherapy or improving a nutritional status during cancer chemotherapy, thereby completing the present invention:

(a) an antioxidant agent;
(b) at least one component selected from the group consisting of vitamin $B_1$, vitamin $B_2$, vitamin $B_6$, niacin, and pantothenic acid;
(c) at least one component selected from the group consisting of folic acid, vitamin $B_{12}$, and vitamin A;
(d) zinc;
(e) selenium; and
(f) coenzyme Q10.

The present invention is summarized as follows:

(1) A composition for reducing oxidative stress and/or side effects occurring during cancer chemotherapy or improving a nutritional status during cancer chemotherapy, comprising the following components (a) to (f):
(a) an antioxidant agent;
(b) at least one component selected from the group consisting of vitamin $B_1$, vitamin $B_2$, vitamin $B_6$, niacin, and pantothenic acid;
(c) at least one component selected from the group consisting of folic acid, vitamin $B_{12}$, and vitamin A;
(d) zinc;
(e) selenium; and
(f) coenzyme Q10.
(2) The composition according to (1), wherein the antioxidant agent is an antioxidant vitamin.
(3) The composition according to (2), wherein the antioxidant vitamin is at least one member selected from the group consisting of vitamin C, vitamin E, and β-carotene.
(4) The composition according to any of (1) to (3), further comprising vitamin $D_3$ and/or iron.
(5) The composition according to any of (1) to (4), comprising vitamin C, vitamin E, β-carotene, vitamin $B_1$, vitamin $B_2$, vitamin $B_6$, niacin, pantothenic acid, folic acid, vitamin $B_{12}$, vitamin A, zinc, selenium, coenzyme Q10, vitamin $D_3$, and iron.
(6) The composition according to (5), comprising, per dosage unit, 500±100 mg of vitamin C, 20±4 mg of vitamin E, 6.6±1.32 mg of β-carotene, 3±0.6 mg of vitamin $B_1$, 3±0.6 mg of vitamin $B_2$, 5±1 mg of vitamin $B_6$, 15±3 mg of niacin, 10±2 mg of pantothenic acid, 800±160 mg of folic acid, 10±2 mg of vitamin $B_{12}$, 550±110 μg of vitamin A (retinol equivalent), 10±2 mg of zinc, 50±10 μg of selenium, 15±3 mg of coenzyme Q10, 3.7±0.74 μg of vitamin $D_3$, and 5±1 mg of iron, and having an energy of 80±16 kcal.
(7) The composition according to any of (1) to (6), further comprising biotin, galacto-oligosaccharide, potassium, calcium, magnesium, and phosphorus.
(8) The composition according to (7), comprising, per dosage unit, 50±10 μg of biotin, 2±0.4 g of galacto-oligosaccharide, 90±18 mg of potassium, 70±14 mg of calcium, 3±0.6 mg of magnesium, and 30±6 mg of phosphorus.
(9) The composition according to any of (1) to (8), being dispersed in a liquid that can be taken.
(10) The composition according to (9), wherein the liquid is fruit juice.
(11) The composition according to (9) or (10), having a volume of 125±25 mL per dosage unit.
(12) A method for reducing oxidative stress and/or side effects occurring during cancer chemotherapy or improving a nutritional status during cancer chemotherapy, comprising administering to a subject the following components (a) to (f) in amounts effective for reducing oxidative stress and/or side effects occurring during cancer chemotherapy or improving a nutritional status during cancer chemotherapy:
(a) an antioxidant agent;
(b) at least one component selected from the group consisting of vitamin $B_1$, vitamin $B_2$, vitamin $B_6$, niacin, and pantothenic acid;
(c) at least one component selected from the group consisting of folic acid, vitamin $B_{12}$, and vitamin A;
(d) zinc;
(e) selenium; and
(f) coenzyme Q10.

(13) Use of the following components (a) to (f) for production of a composition for reducing oxidative stress and/or side effects occurring during cancer chemotherapy or improving a nutritional status during cancer chemotherapy:
(a) an antioxidant agent;
(b) at least one component selected from the group consisting of vitamin $B_1$, vitamin $B_2$, vitamin $B_6$, niacin, and pantothenic acid;
(c) at least one component selected from the group consisting of folic acid, vitamin $B_{12}$, and vitamin A;
(d) zinc;
(e) selenium; and
(f) coenzyme Q10.

(14) A composition to be used for reducing oxidative stress and/or side effects occurring during cancer chemotherapy or improving a nutritional status during cancer chemotherapy, comprising the following components (a) to (f):
(a) an antioxidant agent;
(b) at least one component selected from the group consisting of vitamin $B_1$, vitamin $B_2$, vitamin $B_6$, niacin, and pantothenic acid;
(c) at least one component selected from the group consisting of folic acid, vitamin $B_{12}$, and vitamin A;
(d) zinc;
(e) selenium; and
(f) coenzyme Q10.

Advantage of the Invention

By means of the composition according to the present invention, oxidative stress and/or side effects occurring during cancer chemotherapy can be reduced or a nutritional status during cancer chemotherapy can be improved.

The present specification encompasses the description set forth in the specification and/or drawings of Japanese Patent Application No. 2008-001801, based on which the present application claims priority.

BEST MODE FOR CARRYING OUT THE INVENTION

Figure 1A:
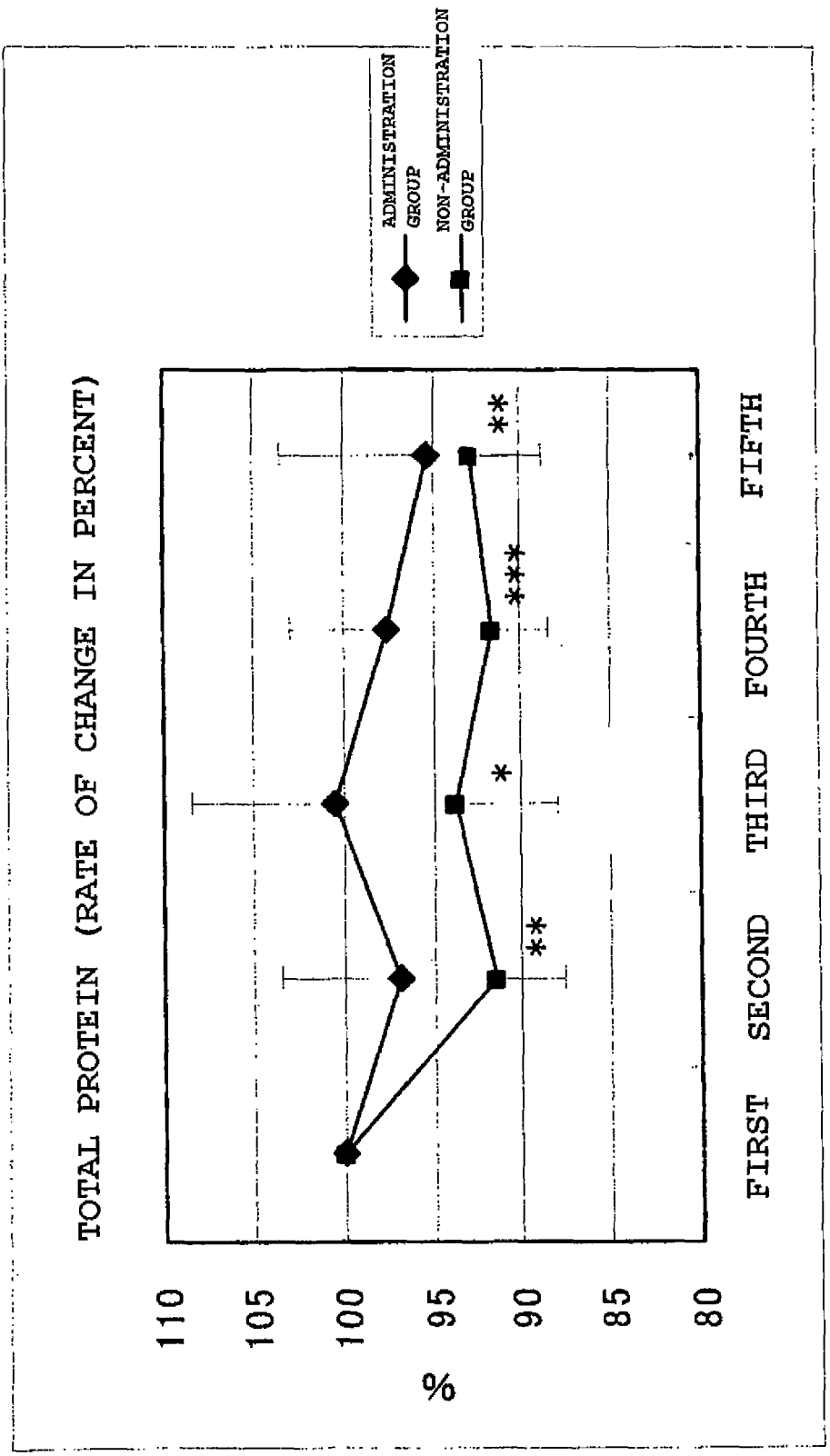
FIG. 1A shows the results of measurement of the total protein (rate of change). A diamond ♦ represents the administration group, and a square ■ represents the non-administration group. Rates of change, which were obtained by setting first measurement values at 100%, were averaged out for each group and the values thus obtained were graphed. The vertical axis represents %, and the horizontal axis represents the respective times of measurement. A value for which a significant difference was observed with respect to the first measurement value is indicated by *, , or * in each group (* means $p<0.05$,  means $p<0.01$, and * means $p<0.001$). In the non-administration group, total protein, which was a nutrition index, was significantly decreased at the second and subsequent measurements with respect to the first measurement value.

Hereinafter, embodiments of the present invention will be described in more detail.

The present invention provides a composition for reducing oxidative stress and/or side effects occurring during cancer chemotherapy or improving a nutritional status during cancer chemotherapy, comprising the following components (a) to (f):

(a) an antioxidant agent;
(b) at least one component selected from the group consisting of vitamin $B_1$, vitamin $B_2$, vitamin $B_G$, niacin, and pantothenic acid;
(c) at least one component selected from the group consisting of folic acid, vitamin $B_{12}$, and vitamin A;
(d) zinc;
(e) selenium; and
(f) coenzyme Q10.

A composition containing vitamins and a trace element such as zinc and selenium, and further, coenzyme Q10 and the like induces biological functions, for example, promotion of metabolism and an anti-inflammatory action, and reinforces an antioxidant action, whereby oxidative stress and/or side effects occurring during cancer chemotherapy can be reduced, and a nutritional status during cancer chemotherapy can also be improved.

The components in the composition of the present invention are broadly classified the into a group of components involved in removal of active oxygen, a metabolic cofactor, and a cell growth-promoting factor.

An antioxidant agent, zinc, selenium, and coenzyme Q10 comprise a group of components involved in removal of active oxygen. During application of cancer chemotherapy, because active oxygen attributable to a biological damage caused by chemotherapy is produced in abundance, consumption of an antioxidant that captures the active oxygen thus produced is increased. The above-described components that are involved in removal of active oxygen play an important role in lessening the consumption of antioxidants.

An antioxidant agent has a strong reducing action on oxidative stress attributable to a biological damage caused by chemotherapy. Examples of the antioxidant agent described as above include antioxidant vitamins such as vitamin C, vitamin E, and β-carotene. Antioxidant vitamins such as vitamin E and vitamin C can exist in a reduced form or an oxidized form, and they oxidize themselves by accepting free radicals from active oxygen, thereby functioning to remove active oxygen. Because these antioxidant vitamins act at different stages, it is preferable to use them simultaneously, rather than using any of them alone. The intake amount of vitamins varies depending on the diet, and particularly, patients requiring dietary restriction tend to be deficient in vitamin intake. In view of the above, it is desirable that the composition of the present invention contain a plurality of antioxidant vitamins in combination. Further, vitamin C, which is one of the above-described antioxidant vitamins, not only functions as an antioxidant agent but is directly involved in over-activation of cAMP and solubilization of lipid, and has various actions such as collagen formation, detoxification of a foreign substance in a living body, induction of interferon production, an antihistamine action, enhancement of immune function, an antiviral action, and an antibacterial action. Therefore, it is preferable to incorporate at least vitamin C as an antioxidant vitamin. It is to be noted that although the above-described antioxidant vitamin agents have been shown as preferable embodiments of the above-described antioxidant agents, the antioxidant agents are not limited to the antioxidant vitamin agents, and an antioxidant substance contained in food and the like such as polyphenol and catechin can be used instead of or as supplements to the above-described antioxidant vitamin agents.

Selenium is a constitutive substance of glutathione peroxidase which is an antioxidant enzyme, and zinc is a constitutive substance of superoxide dismutase which is another antioxidant enzyme.

As coenzyme Q10 has a strong antioxidative action, it is anticipated to exhibit prophylactic and preventive effects on diseases attributable to oxidative stress. Also, because coenzyme Q10 is a component involved in ATP production, an effect for smooth metabolism of nutrients is anticipated by supplementation of coenzyme Q10.

When an antioxidant vitamin is used as an antioxidant agent, the amount to be added to the composition is, in terms of the content per dosage unit, appropriately in the range of 100 mg to 2000 mg, preferably 300 mg to 1000 mg in the case of vitamin C, appropriately in the range of 3 mg to 600 mg, preferably 5 mg to 300 mg in the case of vitamin E, and appropriately in the range of 2.0 mg to 10.0 mg, preferably 5.0 mg to 7.0 mg in the case of β-carotene.

The amount to be added to the composition of the present invention is, in terms of the content per dosage unit, appropriately in the range of 1.2 to 30 mg, preferably 9 to 12 mg for an exemplary case of zinc, and appropriately in the range of 10 to 250 μg, preferably 30 to 60 μg in the case of selenium.

The content of coenzyme Q10 is appropriately 1.0 to 1,000 mg, preferably 2 to 100 mg, per dosage unit.

As a metabolic cofactor to be contained in the composition of the present invention, any or all of vitamin $B_1$, vitamin $B_2$, vitamin $B_6$, vitamin $B_{12}$, niacin, pantothenic acid, and folic acid can be added. These vitamins that assist in metabolism have a role as a coenzyme associated with the metabolism of saccharides, lipids, and amino acids, and are important components for the vital activity of life. For example, vitamin $B_1$ is involved in regulation of glycolysis, TCA cycle, and β-oxidation as thiamine pyrophosphate (TPP) and vitamin $B_2$ is involved in the above-described regulation as flavin mononucleotide (FMN) and flavin-adenine dinucleotide (FAD). Vitamin $B_6$ is involved in amino acid metabolism as pyridoxal phosphate and the like. Niacin is involved in glycolysis and lipid metabolism as NAD and NADP. Also, pantothenic acid is involved in the TCA cycle, amino acid metabolism, and lipid metabolism as CoA. Folic acid participates in amino acid metabolism and nucleic acid metabolism as FH4. Vitamin $B_{12}$ is involved in amino acid metabolism as C0B12.

Accordingly, these vitamins are components that constitute a different coenzymes, so it is preferable to use all of these of vitamins as the above-described metabolic cofactor. Particularly, the intake amount of these vitamins varies depending on the amounts of energy and protein intake, and the intake amount of these vitamins tends to be generally insufficient in patients such as patients under cancer chemotherapy who can take in only small amounts of food or those who suffer from reduced absorption rates or utilization rates. Therefore, in order to ensure that intracellular an energy supply as required for wound healing and the like is efficiently carried out in those patients, it is preferable to add all members of the above-described group of vitamins into the composition.

The amount of the above-described vitamins to be added to the composition is, in terms of the content per dosage unit, appropriately in the range of 0.5 to 10 mg, preferably 1.0 to 5.0 mg in the case of vitamin $B_1$, appropriately in the range of 0.5 to 20 mg, preferably 1 to 10 mg in the case of vitamin $B_2$, appropriately in the range of 1.6 to 60.0 mg, preferably 3.0 to 8.0 mg in the case of vitamin $B_6$, appropriately in the range of 1.1 to 50.0 μg, preferably 5.0 to 15.0 μg in the case of vitamin $B_{12}$, appropriately in the range of 1 to 100 mg, preferably 5 to 50 mg in the case of niacin, appropriately in the range of 200 mg to 1.1 mg, preferably 600 to 1,000 μg in the case of folic acid, and appropriately in the range of 1 to 100 mg, preferably 5 to 50 mg in the case of pantothenic acid.

Further, a cell growth-promoting factor to be contained in the composition of the present invention is a factor capable of promoting cell differentiation and proliferation. As the cell growth-promoting factor, folic acid, vitamin $B_{12}$, vitamin A, and the like may be mentioned as examples, and any or all of these can be used. Folic acid and vitamin $B_{12}$ not only function as metabolic cofactors in a living body but also have a function to promote cell differentiation and proliferation. Also, vitamin A has a function to promote cell differentiation and proliferation, besides its function as an antioxidant vitamin. Since proliferation of an immune cell such as a T-cell can also be promoted by promoting cell proliferation and differentiation, immunity can be improved to strengthen defense against an infection.

The amount of each component to be added to the composition is, in terms of the content per dosage unit, as described above with respect to folic acid and vitamin $B_{12}$, while the amount of vitamin A (retinol equivalent) to be added is appropriately 10 μg to 3,000 μg, preferably 100 μg to 550 μg.

Furthermore, other additional substances can be supplemented besides the above-described components. For example, considering that patients such as patients under cancer chemotherapy who can take in only small amounts of food develop iron deficiency and the like, addition of iron to the composition is also possible. Because iron is a constitutive component of hemoglobin, there is a risk for developing anemia if iron is deficient. Prophylactic, preventive, and improving effects on an anemic symptom are anticipated with incorporation of iron. Also, calcium as well as vitamin D which promotes calcium absorption (for example, vitamin $D_3$), and the like can be added. Furthermore, an intestinal regulation substance, for example, raffinose, can be added. Per dosage unit of the composition of the present invention, the content of iron is appropriately 0.5 to 50 mg, preferably 1.0 to 30 mg and the content of vitamin $D_3$ is appropriately 1.0 μg to 10.0 μg, preferably 2.0 μg to 8.0 μg.

A preferred embodiment of the present invention is a composition containing vitamin C, vitamin E, β-carotene, vitamin $B_1$, vitamin $B_2$, vitamin $B_6$, niacin, pantothenic acid, folic acid, vitamin $B_{12}$, vitamin A, zinc, selenium, coenzyme Q10, vitamin $D_3$, and iron. A more preferred embodiment of the present invention is a composition comprising, per dosage unit, 500±100 mg of vitamin C, 20±4 mg of vitamin E, 6.6±1.32 mg of β-carotene, 3±0.6 mg of vitamin $B_1$, 3±0.6 mg of vitamin $B_2$, 5±1 mg of vitamin $B_6$, 15±3 mg of niacin, 10±2 mg of pantothenic acid, 800±160 μg of folic acid, 10±2 μg of vitamin $B_{12}$, 550±110 μg of vitamin A (retinol equivalent), 10±2 mg of zinc, 50±10 μg of selenium, 15±3 mg of coenzyme Q10, 3.7±0.74 μg of vitamin $D_3$, and 5±1 mg of iron, and having an energy of 80±16 kcal.

The composition of the present invention can further contain α-lipoic acid and/or chromium.

The α-lipoic acid is involved in promotion of a glucose metabolism. It is considered that α-lipoic acid stimulates mobilization of an intracellular glucose transporter (GLUT-4) to a cellular membrane, whereby the amount of glucose uptake mediated by insulin in muscle and a myocyte is considerably increased.

The content of α-lipoic acid is, for example, appropriately 20 to 1,000 mg, preferably 25 to 100 mg, per dosage unit.

Chromium increases insulin sensitivity by enhancing the insulin receptor, binding capacity, increasing the number of insulin receptors, and enhancing insulin receptor kinase activity.

The content of chromium is, for example, appropriately 5 to 50 μg, preferably 10 to 40 n, per dosage unit.

The composition of the present invention can further contain other components besides the above-described components. For example, the composition of the present invention can contain biotin, galacto-oligosaccharide, potassium, calcium, magnesium, phosphorus, and the like. Deficiency of a certain component in a restricted diet such as a patient's diet can be prevented by incorporating the above-described components in the composition of the present invention.

The content of biotin, for example, in the composition of the present is, per dosage unit, appropriately 1 to 200 μg, preferably 10 to 100 μg, the content of galacto-oligosaccharide is appropriately 0.1 to 20 g, preferably 1 to 10 g, the content of potassium is appropriately 10 to 1,000 mg, preferably 15 to 500 mg, the content of calcium is appropriately 1 to 2,300 mg, preferably 10 to 600 mg, the content of magnesium is appropriately 0.1 to 10 mg, preferably 1 to 5 mg, and the content of phosphorus is appropriately 1 to 3500 mg, preferably 5 to 1050 mg.

A preferred embodiment of the present invention is a composition containing, per dosage unit, 50±10 μg of biotin, 2±0.4 g of galacto-oligosaccharide, 90±18 mg of potassium, 70±14 mg of calcium, 3±0.6 mg of magnesium, and 30±6 mg of phosphorus.

The amount of energy in the composition of the present invention is appropriately 5 kcal to 200 kcal, preferably 20 kcal to 150 kcal, per dosage unit. Also, with regard to general components, the content of protein, for example, may be approximately 0.4±0.08 g or approximately 0.7±0.14 g, the content of carbohydrate may be approximately 11.1±2.22 g or approximately 21.2±4.24 g, and the content of sodium may be approximately 30±6 mg, per dosage unit.

The composition of the present invention may be prepared in accordance with a method well known to a person skilled in the art. For example, the above-described components can be mixed and prepared into such dosage forms as powder, granule, tablet, and liquid. A liquid is a more preferable dosage form because it can be administered through a tube to a patient having a difficulty with oral intake.

When the composition of the present invention is prepared as a liquid, the liquid medium in which the composition is dispersed or dissolved is not particularly limited as long as it is a commonly administered liquid medium and does not reduce an action to be exhibited by each component on a living body. For example, water and physiological saline can be used. For oral administration, fruit juice may be used to improve taste. Examples of the fruit juice include blueberry juice, grape juice, grapefruit juice, lemon juice, orange juice, carrot juice, apple juice, and pineapple juice. Among them, carrot juice, blueberry juice, and grape juice are preferable for the reason that the sourness and odor of vitamin C and a group of B vitamins can be relieved. In the case of a liquid, the volume is appropriately 10 to 250 ml, preferably 50 to 200 ml, and more preferably 125±25 ml, per dosage unit. Also, in the case of a liquid, the water content may be, for example, approximately 116±23.2 g or approximately 110±22 g, per dosage unit.

Exemplary table for components in the composition of the present invention (in 125±25 mL) are shown in Table 1 below.

TABLE 1

| | | Composition A | Composition B |
|---|---|---|---|
| Energy | | 80 ± 16 kcal | 46 ± 9.2 kcal |
| General components | Protein | 0.7 ± 0.14 g | 0.4 ± 0.08 g |
| | Lipid | 0 g | 0 g |
| | Carbohydrate | 21.2 ± 4.24 g | 11.1 ± 2.22 g |
| | Sodium | 30 ± 6 mg | 30 ± 6 mg |
| Minerals | Potassium | 90 ± 18 mg | 40 ± 8 mg |
| | Calcium | 70 ± 14 mg | 80 ± 16 mg |
| | Magnesium | 3 ± 0.6 mg | 3 ± 0.6 mg |
| | Phosphorus | 30 ± 6 mg | 7.5 ± 1.5 mg |
| Trace elements | Iron | 5 ± 1 mg | 0 mg |
| | Zinc | 10 ± 2 mg | 10 ± 2 mg |
| | Copper | 0.01 ± 0.002 mg | 0 mg |
| | Selenium | 50 ± 10 μg | 50 ± 10 μg |
| | Chromium | — | 30 ± 6 μg |
| Vitamins | Vitamin A (retinol equivalent) | 550 ± 110 μg | 300 μg ± 60 μg |
| | β-carotene | 6.6 ± 1.32 mg | — |
| | Vitamin $B_1$ | 3 ± 0.6 mg | 3 ± 0.6 mg |
| | Vitamin $B_2$ | 3 ± 0.6 mg | 3 ± 0.6 mg |
| | Vitamin $B_6$ | 5 ± 1 mg | 5 ± 1 mg |
| | Vitamin $B_{12}$ | 10 ± 2 μg | 10 ± 2 μg |
| | Vitamin C | 500 ± 100 mg | 500 ± 100 mg |
| | Niacin | 15 ± 3 mg | 15 ± 3 mg |
| | Folic acid | 800 ± 160 μg | 800 ± 160 μg |
| | Vitamin $D_3$ | 3.7 ± 0.74 μg | 5 ± 1 μg |
| | Vitamin E | 20 ± 4 mg | 20 ± 4 mg |
| | Biotin | 50 ± 10 μg | 50 ± 10 μg |
| | Pantothenic acid | 10 ± 2 mg | 10 ± 2 mg |
| Coenzyme Q10 | | 15 ± 3 mg | — |
| α-lipoic acid | | — | 30 ± 6 mg |
| Galacto-oligosaccharide | | 2 ± 0.4 g | 2 ± 0.4 g |
| Water | | 110 ± 22 g | 116 ± 23.2 g |

A reducing effect on oxidative stress and/or side effects occurring during cancer chemotherapy or an improving effect on a nutritional status during cancer chemotherapy, both being exhibited by the composition prepared as above can be confirmed by conducting a biochemical examination (for example, erythrocyte count, leukocyte count, leukocyte fraction, lymphocyte count, platelet count, total protein, albumin, blood glucose level, total cholesterol, triglyceride, CRP, Hb, prealbumin, radical-generating capacity, lipid peroxide, antioxidant vitamins (VA, VC, VE), Zn, and the like), QOL evaluation based on a survey (for example, the presence or absence of stomatitis, anorexia, nausea, vomiting, a feeling of fatigue, and diarrhea, and frequency of development of side effects and the like, both before and after administration of the composition to candidate patients for cancer chemotherapy, and then observing any differences between values measured before and after administration. Alternatively, a value measured in a group to which the composition has been administered and a value measured in a group to which a placebo (for example, a commercially available drink) has been administered (control group) can be compared.

A standard level of each of the above substances in the blood is as follows; 4.4 million to 5.4 million erythrocytes/mm3 (male) and 3.8 million to 4.6 million erythrocytes/mm3 (female); 4000 to 8000 leukocytes/μl; a leukocyte fraction containing 3 to 6% of stab neutrophils, 45 to 55% of segmented neutrophils, 1 to 5% of eosinophils, 0 to 1% of basophils, 25 to 45% of lymphocytes, and 4 to 7% of monocytes; 1500 to 3000 total lymphocytes mm3; 130 thousand to 400 thousand platelets/4; 6.5 to 8.2 g total protein/dl; 3.5 to 5.0 g albumin/dl; a fasting blood glucose level of 70 to 110 mg/dl; 120 to 220 mg total cholesterol/dl; 40 to 150 mg triglyceride/dl; 0 to 0.2 mg CRP/dl; 14 to 18 g Hb/dl; 10 to 40 mg prealbumin/dl; a radical-generating capacity of 0.0 to 1.3 nmol/ml; lipid peroxide; an antioxidant vitamin of 60 to 320 IU VA/dl, 0.5 to 1.4 mg VC/dl, and 0.6 to 2.4 mg VE/dl; and 70 to 140 μg Zn/dl. If, as a result of a biochemical examination of patients administered with the composition of the present invention, measured values are found to be within the above-described ranges, it can be said that oxidative stress occurring during cancer chemotherapy has been reduced or a nutritional status during cancer chemotherapy improved.

As described above, the composition of the present invention can be used for reducing oxidative stress and/or side effects occurring during cancer chemotherapy or improving a nutritional status during cancer chemotherapy. The composition of the present invention is advantageously administered to a candidate patient for cancer chemotherapy in a dose of one dosage unit per day. The composition of the present invention is advantageously administered orally or through a tube.

EXAMPLES

Hereinafter, the present invention will be specifically described with Examples. It is to be noted that the Examples are provided to illustrate the present invention, not to limit the scope of the present invention.

Preparation Example 1

Preparation of the Composition

The composition prepared was one that contained various kinds of components in a fruit juice liquid containing a carrot extract. One bottle of the composition (125 ml) contains 300 μg of vitamin A (retinal equivalent), 6.6 mg of β-carotene, 3 mg of vitamin B1, 3 mg of vitamin B2, 5 mg of vitamin B6, 10 μg of vitamin B12, 500 mg of vitamin C, 15 mg of niacin, 800 μg of folic acid, 3.7 μg of vitamin D3, 20 mg of vitamin E, 50 mg of biotin, 10 mg of pantothenic acid, 5 mg of iron, 10 mg of zinc, 0.01 mg of copper, 50 μg of selenium, 90 mg of potassium, 70 mg of calcium, 3 mg of magnesium, 30 mg of phosphorus, 30 mg of sodium, 15 mg of coenzyme Q10, and 2.0 g of galacto-oligosaccharide.

Example 1

Usefulness of the Composition

Objective: To administer the composition (prepared in Preparation Example 1) as a vitamin and trace element-supplemented drink to candidate patients with hematologic neoplasm for cancer chemotherapy and to see how it was effective in reducing oxidative stress and side effects occurring during chemotherapy, in improving a nutritional status, and in influencing the patients' QOL.

Research Method

Subjects: Patients with hematologic neoplasm who were scheduled to receive cancer chemotherapy from whom consent was obtained.

Subject product: The composition prepared in Preparation Example 1 (125 mL/bottle)

Administration method: Fresh patients with hematologic neoplasm who were scheduled to receive cancer chemotherapy and from whom consent was obtained are registered, and are assigned to a group in which the composition prepared in Preparation Example 1 is to be consumed (an administration group) and a group in which the composition is not to be consumed (a non-administration group) by an envelope method. In the administration group, one bottle (125 ml) of the composition prepared in Preparation Example 1 is administered per day in addition to a regular diet from the day of initiation of cancer chemotherapy (the day of initiation of a first cycle) until the day of completion of a second cycle. The non-administration group is given only a regular diet.

With regard to a hematological examination, the initiation of cancer chemotherapy (the day before initiation of administration of the composition prepared in Preparation Example 1) is set at day 1, and the examination is conducted at five points including day 1, day 10, day 22 (the day of completion of the first cycle), day 32 (day 10 in the second cycle), and day 43 (the day of completion of the second cycle).

It is to be noted that a meal consumed other than the provided meal is recorded in a "food journal", while the subjects are requested to avoid consumption of supplements such as vitamins and trace elements.

The number of cases: Six cases in the administration group and six cases in the non-administration group (a total of 12 cases).

Items of evaluation before and after administration:

1) Hematological Examination

Erythrocyte count, leukocyte, leukocyte fraction, lymphocyte count, platelet count, total protein, albumin, blood glucose level, total cholesterol, triglyceride, total bilirubin, direct bilirubin, AST, ALT, Al-p, BUN, creatinine, Na, K, Cl, CRP, and Hb 2) Special Examination Prealbumin, radical-generating capacity, lipid peroxide, antioxidant vitamins (VA, VC, and VE), and Zn 3) General Urinalysis Protein (qualitative), glucose (qualitative), and urobilinogen (qualitative)

4) Evaluation of QOL Based on a Survey

Figure 1B:
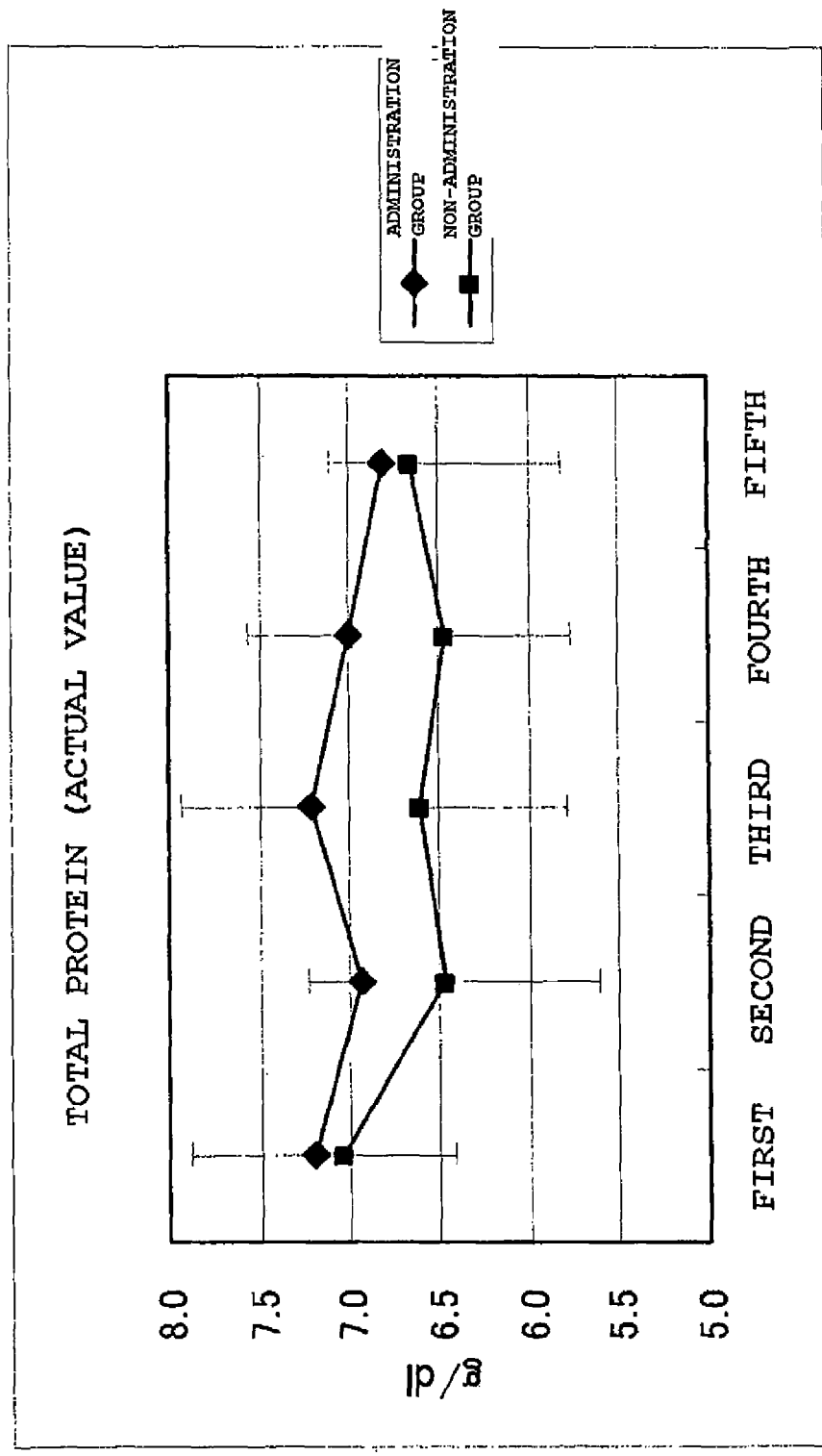
FIG. 1B shows the results of measurement of total protein (actual value). A diamond ♦ represents the administration group, and a square ■ represents the non-administration group. Measurement values were averaged out for each group and the values thus obtained were graphed. The vertical axis represents the concentration of total protein in the blood (g/dl) and the horizontal axis represents the respective times of measurement. No significant difference was observed in the actual values between the two groups.
Figure 2A:
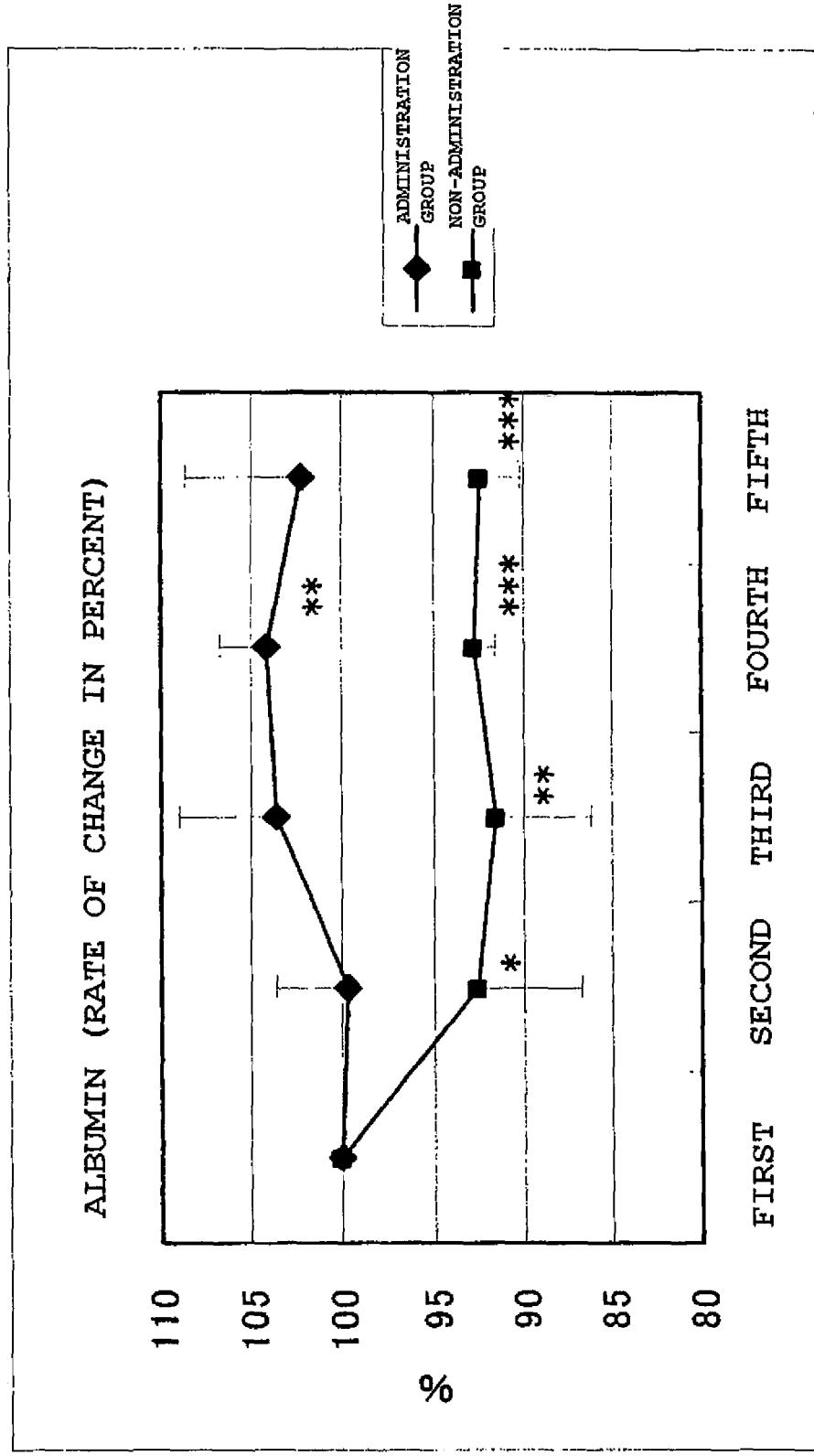
FIG. 2A shows the results of measurement of albumin (rate of change). A diamond ♦ represents the administration group, and a square ■ represents the non-administration group. Rates of change, which were obtained by setting first measurement values at 100%, were averaged out for each group and the values thus obtained were graphed. The vertical axis represents %, and the horizontal axis represents changes over time at each time of measurement. A value for which a significant difference was observed with respect to the first measurement value is indicated by *, , or * in each group (* means $p<0.05$,  means $p<0.01$, and * means $p<0.001$). In the non-administration group, albumin was significantly decreased at the second and subsequent measurements, whereas in the administration group, it was significantly increased.
Figure 2B:
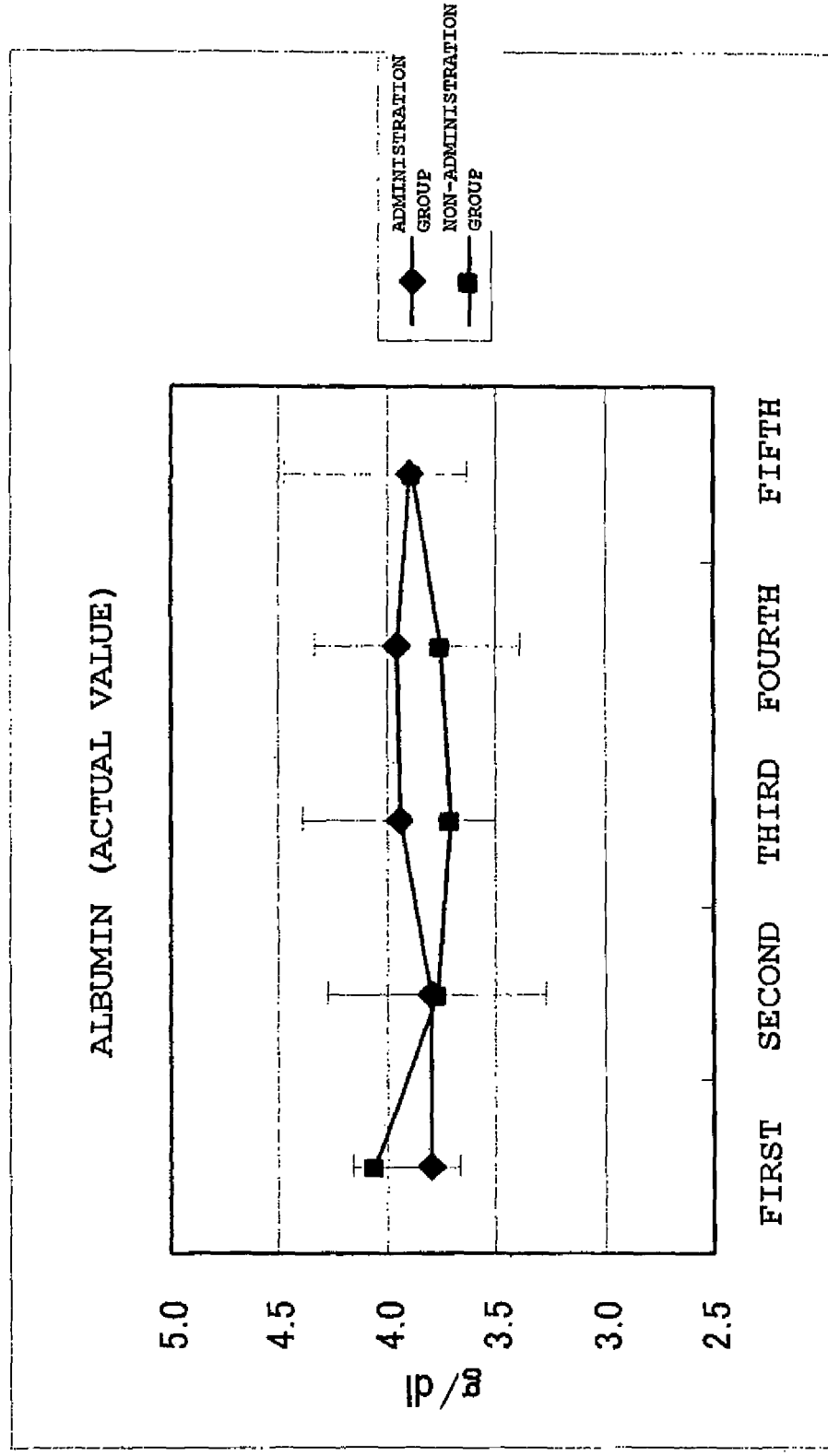
FIG. 2B shows the results of measurement of albumin (actual value). A diamond ♦ represents the administration group, and a square ■ represents the non-administration group. Measurement values were averaged out for each group and the values thus obtained were graphed. The vertical axis represents the concentration of albumin in the blood (g/dl) and the horizontal axis represents the respective times of measurement. For the actual values, fluctuation was within the rouge of normal values, and no significant difference was observed between the two groups.
Figure 3A:
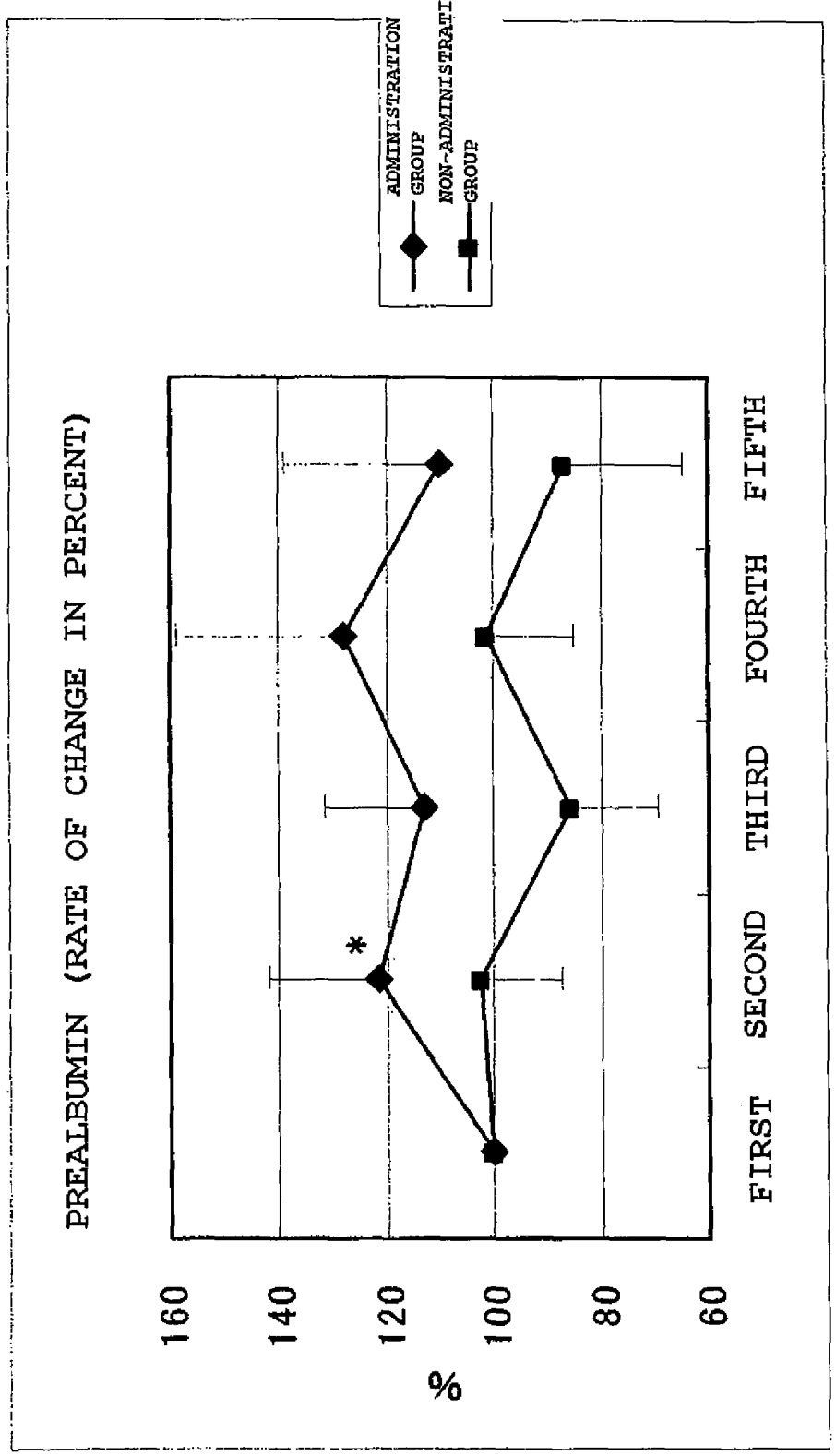
FIG. 3A shows the results of measurement of prealbumin (rate of change). A diamond ♦ represents the administration group, and a square ■ represents the non-administration group. Rates of change, which were obtained by setting first measurement values at 100%, were averaged out for each group and the values thus obtained were graphed. The vertical axis represents %, and the horizontal axis represents changes over time at each time of measurement. A value for which a significant difference was observed with respect to the first measurement value is indicated by * in each group (* means $p<0.05$). An increasing tendency and a decreasing tendency were exhibited in the administration group and the non-administration group, respectively.
Figure 3B:
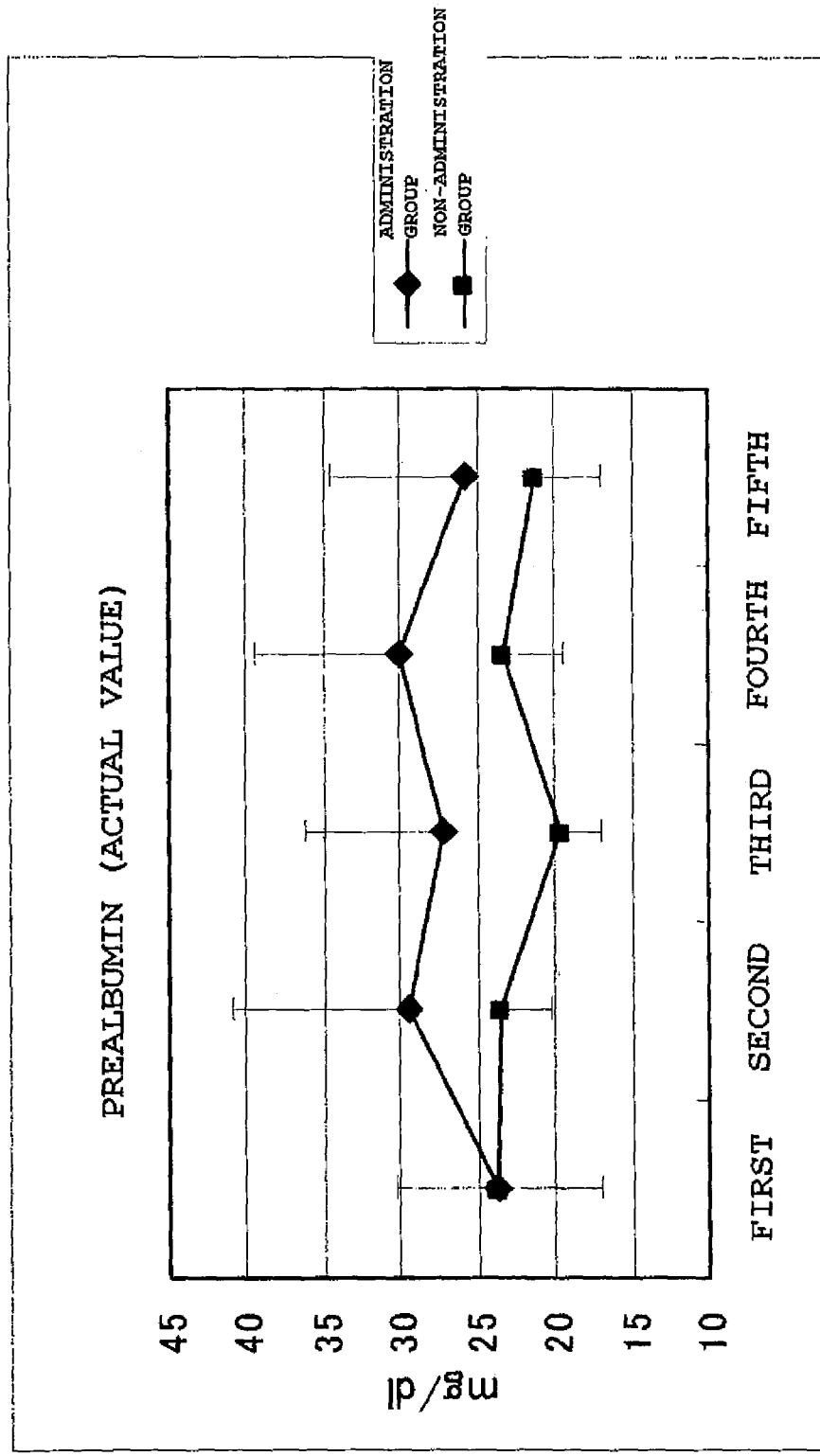
FIG. 3B shows the results of measurement of prealbumin (actual value). A diamond ♦ represents the administration group, and a square ■ represents the non-administration group. Measurement values were averaged out for each group and the values thus obtained were graphed. The vertical axis represents the concentration of prealbumin in the blood (mg/dl) and the horizontal axis represents the times of measurement. For the actual values, no significant difference was observed, but an increasing tendency and a decreasing tendency were exhibited in the administration group and the non-administration group, respectively.
Figure 4A:
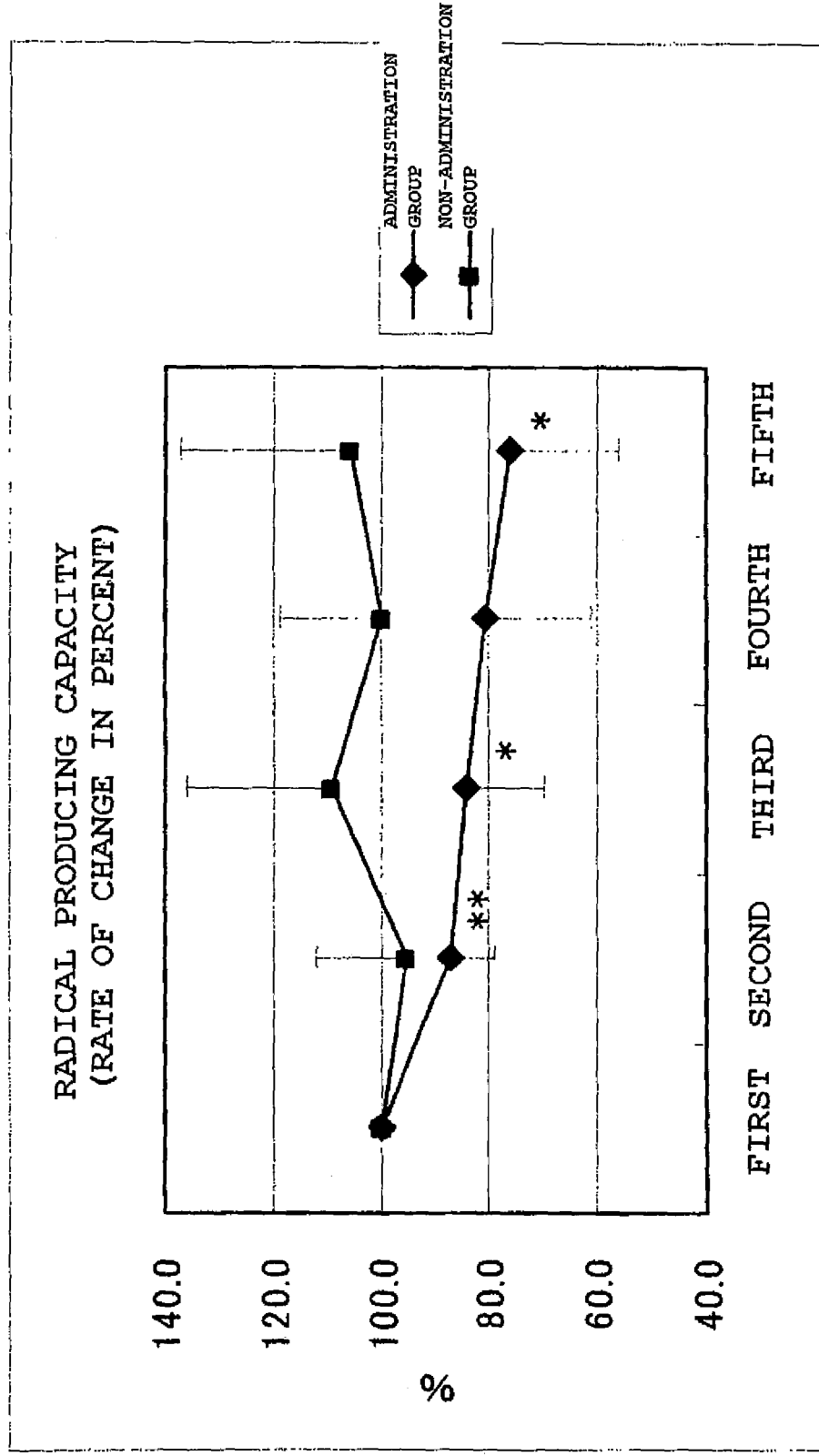
FIG. 4A shows the results of measurement of a radical-generating capacity (rate of change). A diamond ♦ represents the administration group, and a square ■ represents the non-administration group. Rates of change, which were obtained by setting first measurement values at 100%, were averaged out for each group and the values thus obtained were graphed. The vertical axis represents %, and the horizontal axis represents changes over time at each time of measurement. A value for which a significant difference was observed with respect to the first measurement value is indicated by * or ** in each group (* means p<0.05 and ** means p<0.01). In the non-administration group, an increasing tendency of radical-generating capacity was exhibited, whereas in the administration group, the radical-generating capacity was significantly decreased.
Figure 4B:
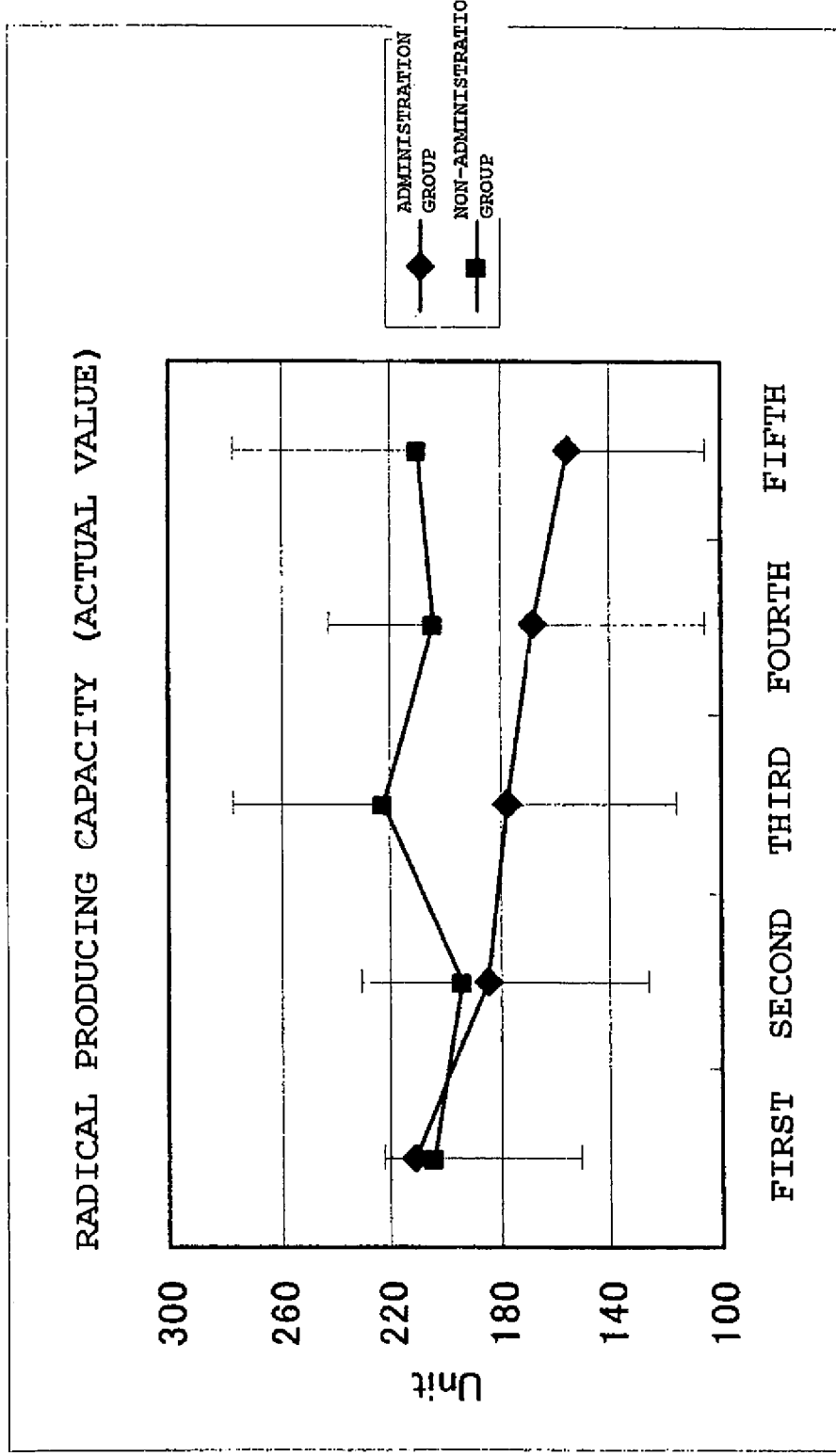
FIG. 4B shows the results of measurement of a radical-generating capacity (actual value). A diamond ♦ represents the administration group, and a square ■ represents the non-administration group. Measurement values were averaged out for each group and the values thus obtained were graphed. The vertical axis represents a radical-generating capacity in the blood (unit) and the horizontal axis represents the times of measurement. An increasing tendency and a decreasing tendency were observed in the non-administration group and the administration group, respectively.
Figure 5A:
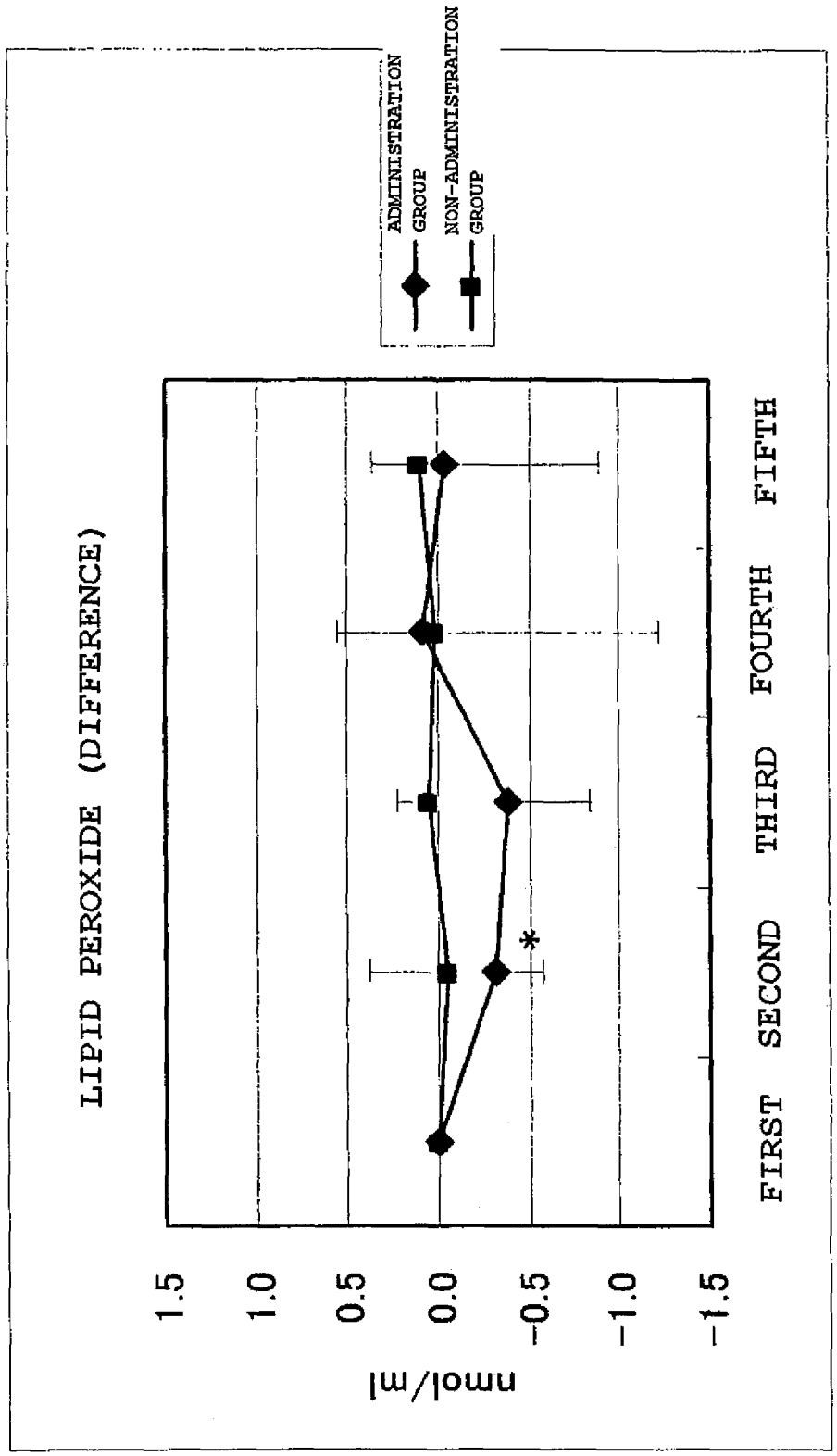
FIG. 5A shows the results of measurement of lipid peroxide (difference). A diamond ♦ represents the administration group, and a square ■ represents the non-administration group. Differences from first measurement values were averaged out for each group and the values thus obtained were graphed. The vertical axis represents nmol/ml, and the horizontal axis represents changes over time at each time of measurement. A value for which a significant difference was observed with respect to the first measurement value is indicated by * in each group (* means p<0.05). A decreasing tendency was observed at the second and third measurements in the administration group.
Figure 5B:
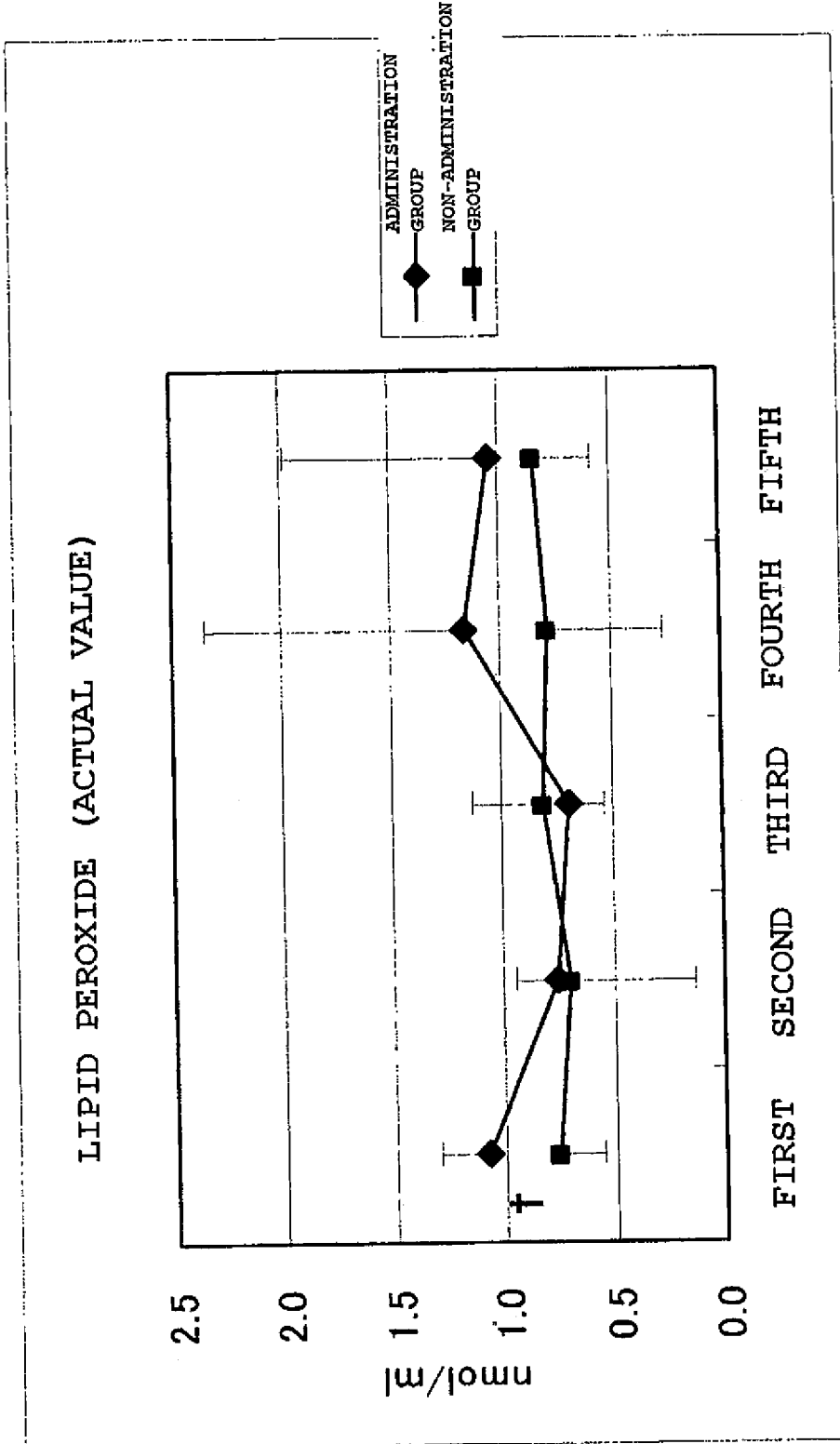
FIG. 5B shows the results of measurement of lipid peroxide (actual value). A diamond ♦ represents the administration group, and a square ■ represents the non-administration group. Measurement values were averaged out for each group and the values thus obtained were graphed. The vertical axis represents Unit, and the horizontal axis represents the times of measurement. There was almost no change in the non-administration group. In the administration group, a decreasing tendency was observed at the second and third measurements, but the value obtained at the fifth measurement was almost the same as the value for the first measurement.
Figure 6A:
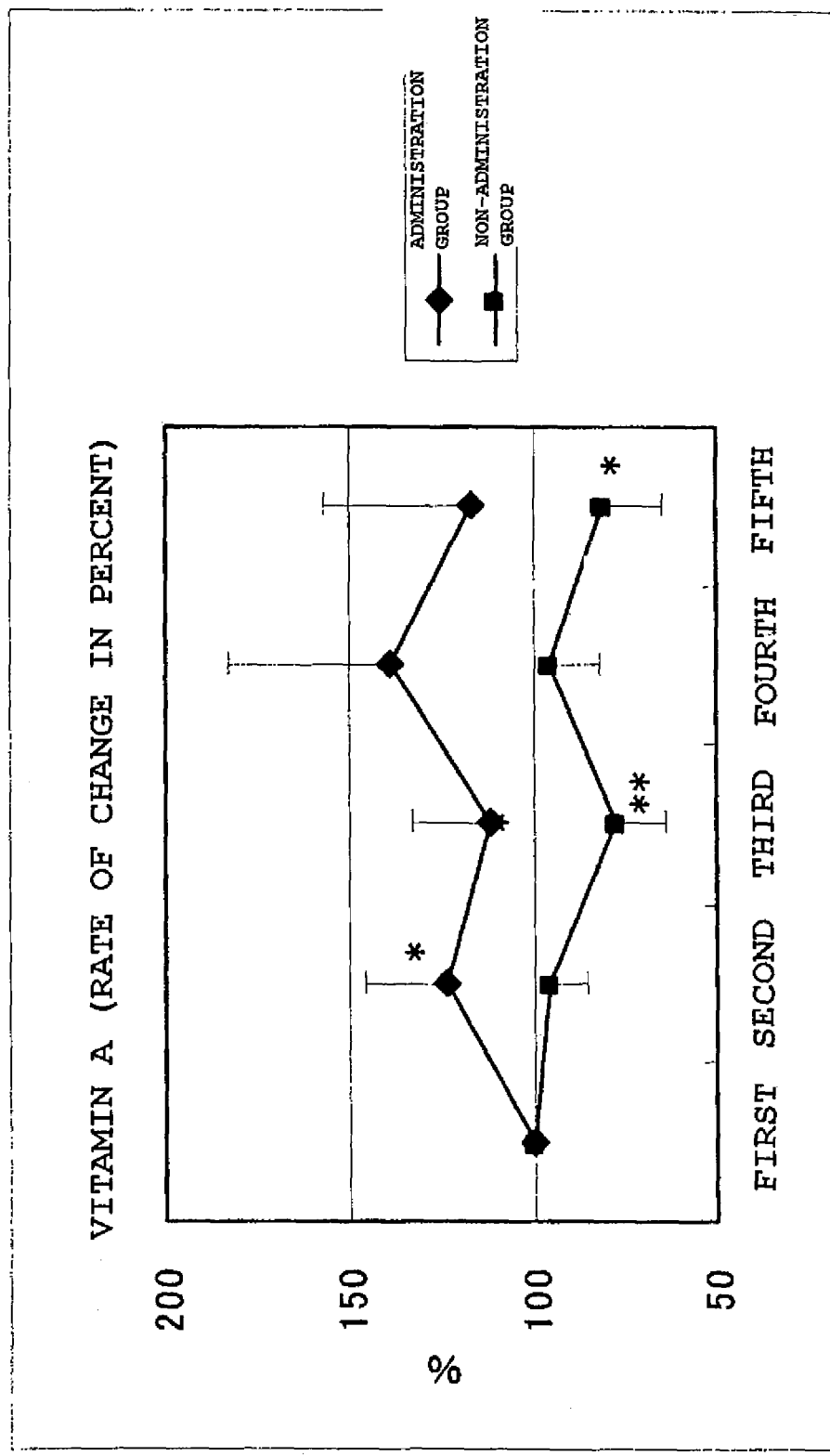
FIG. 6A shows the results of measurement of vitamin A (rate of change). A diamond ♦ represents the administration group, and a square ■ represents the non-administration group. Rates of change, which were obtained by setting first measurement values at 100%, were averaged out for each group and the values thus obtained were graphed with respect to each group. The vertical axis represents %, and the horizontal axis represents changes over time at each time of measurement. A value for which a significant difference was observed with respect to the first measurement value is indicated by * or ** in each group (* means p<0.05 and ** means p<0.01). The rate of change of vitamin A was significantly increased in the administration group, whereas it was significantly decreased in the non-administration group.
Figure 6B:
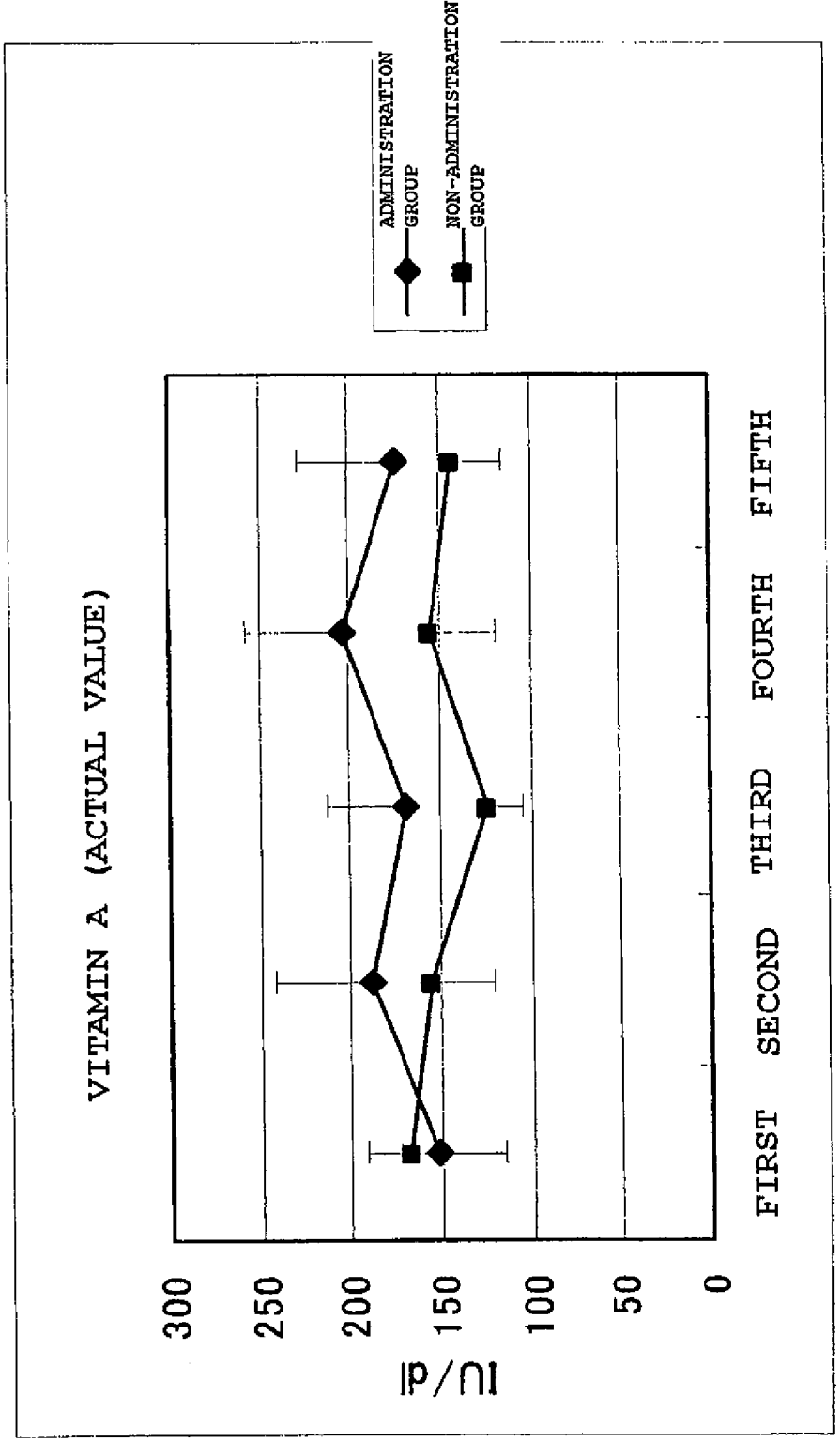
FIG. 6B shows the results of measurement of vitamin A (actual value). A diamond ♦ represents the administration group, and a square ■ represents the non-administration group. Measurement values were averaged out for each group and the values thus obtained were graphed. The vertical axis represents the concentration of vitamin A in the blood (IU/dl) and the horizontal axis represents the respective times of measurement. A decreasing tendency and an increasing tendency were observed in the non-administration group and the administration group, respectively.
Figure 7A:
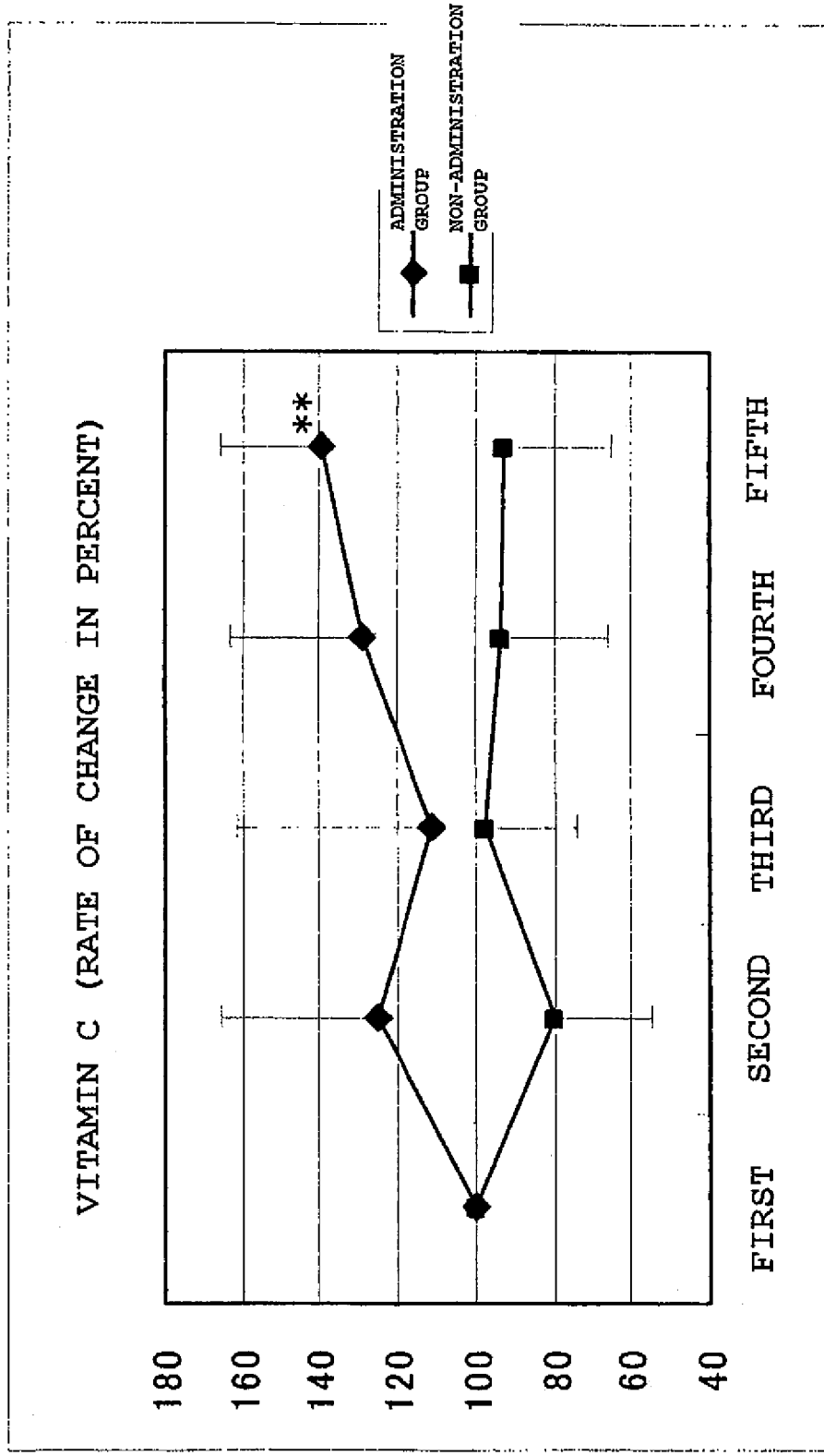
FIG. 7A shows the results of measurement of vitamin C (rate of change). A diamond ♦ represents the administration group, and a square ■ represents the non-administration group. Rates of change, which were obtained by setting first measurement values at 100%, were averaged out for each group and the values thus obtained were graphed. The vertical axis represents %, and the horizontal axis represents changes over time at each time of measurement. A value for which a significant difference was observed with respect to the first measurement value is indicated by  in each group ( means p<0.01). While there was almost no change in the non-administration group, the rate of change of vitamin C was significantly increased in the administration group.
Figure 7B:
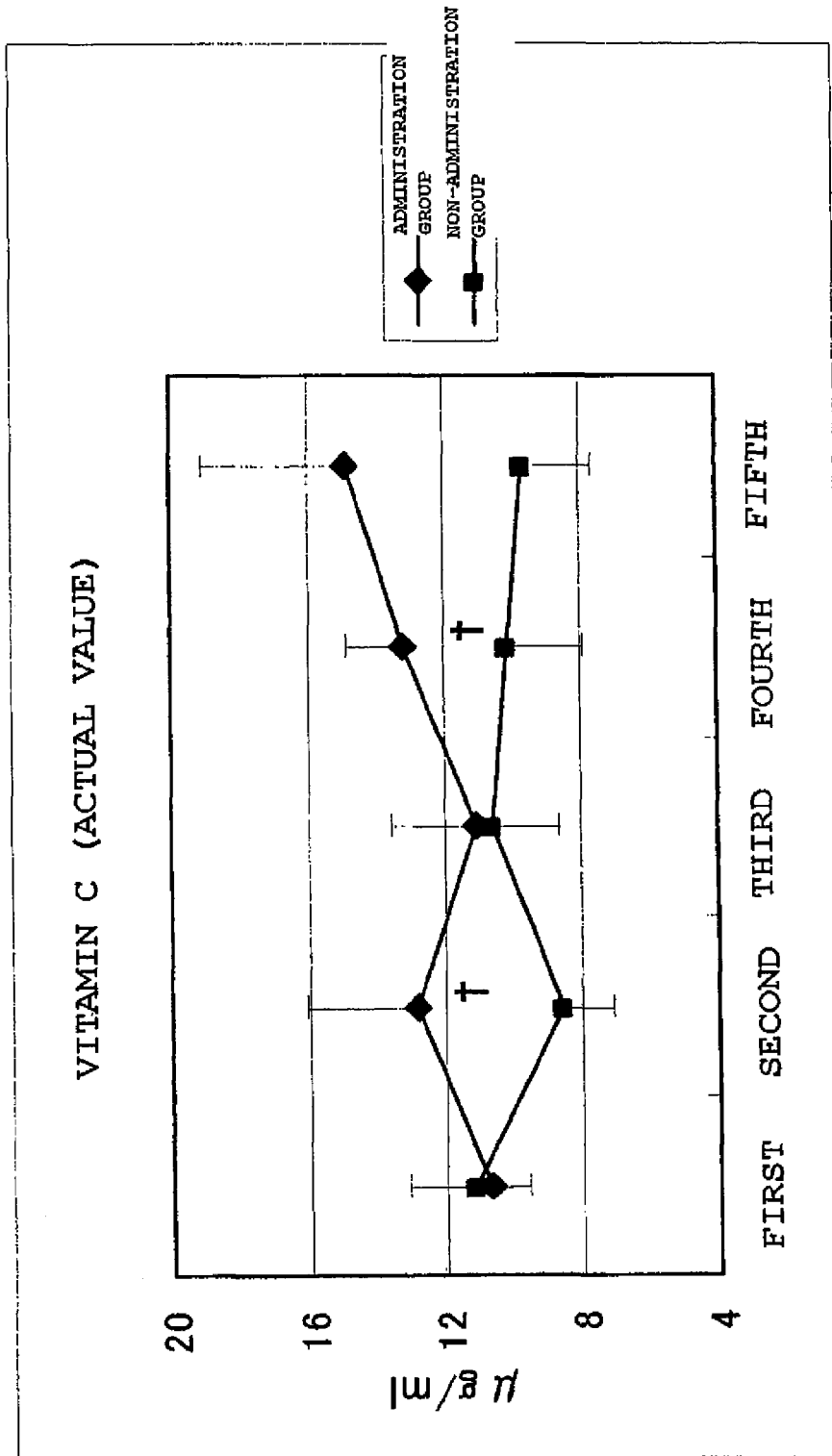
FIG. 7B shows the results of measurement of vitamin C (actual value). A diamond ♦ represents the administration group, and a square ■ represents the non-administration group. Measurement values were averaged out for each group and the values thus obtained were graphed. The vertical axis represents the concentration of vitamin C in the blood (µg/ml), and the horizontal axis represents the respective times of measurement. An increasing tendency was exhibited in the administration group, with a significant increase at the second and fourth measurements as compared with the non-administration group. A value for which a significant difference (p<0.05) was observed between the two groups is indicated by †.
Figure 8A:
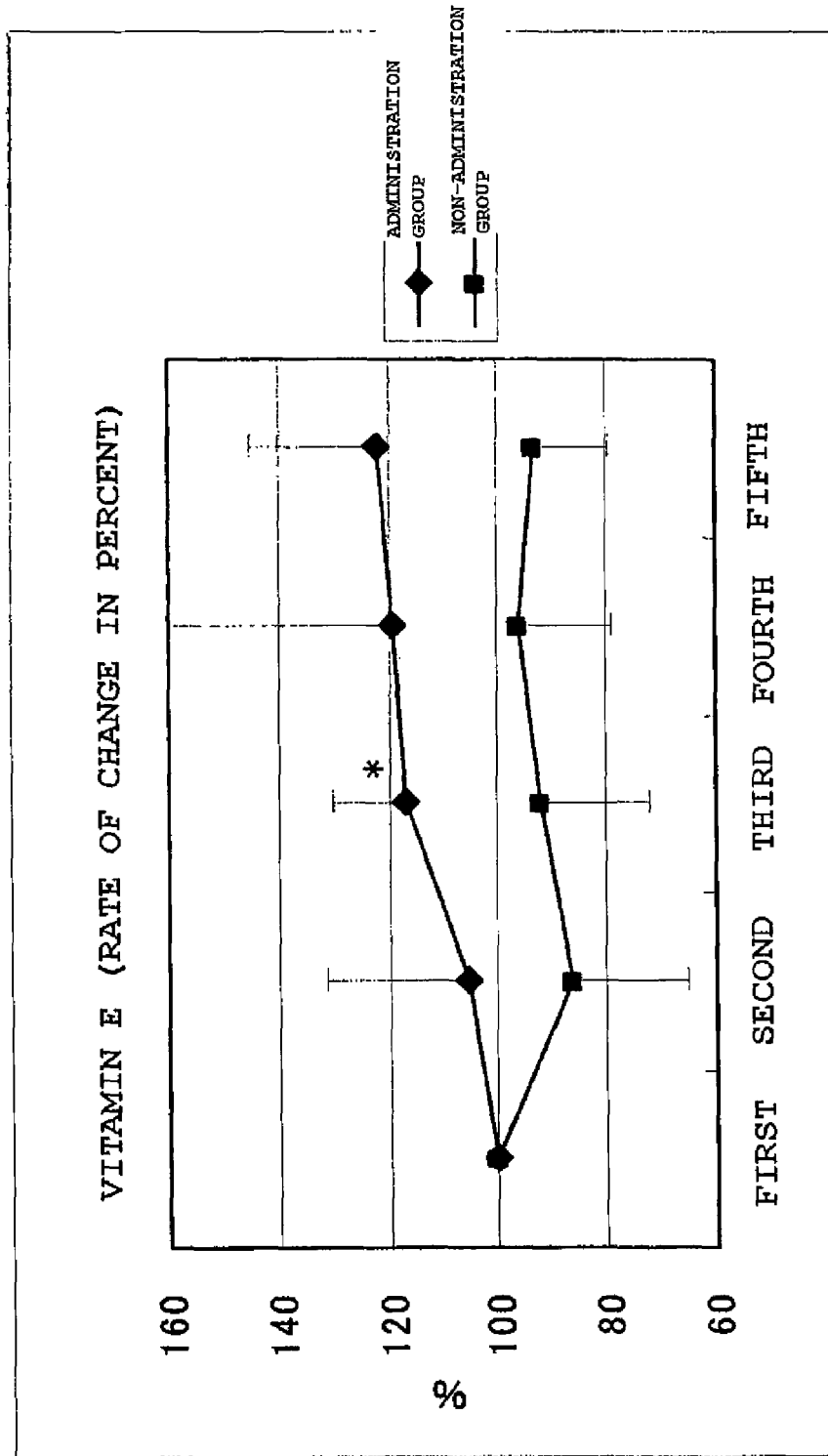
FIG. 8A shows the results of measurement of vitamin E (rate of change). A diamond ♦ represents the administration group, and a square ■ represents the non-administration group. Rates of change, which were obtained by setting first measurement values at 100%, were averaged out for each group and the values thus obtained were graphed. The vertical axis represents %, and the horizontal axis represents changes over time at each time of measurement. A value for which a significant difference was observed with respect to the first measurement value is indicated by in each group (* means p<0.05). The rate of change of vitamin E was significantly increased in the administration group.
Figure 8B:
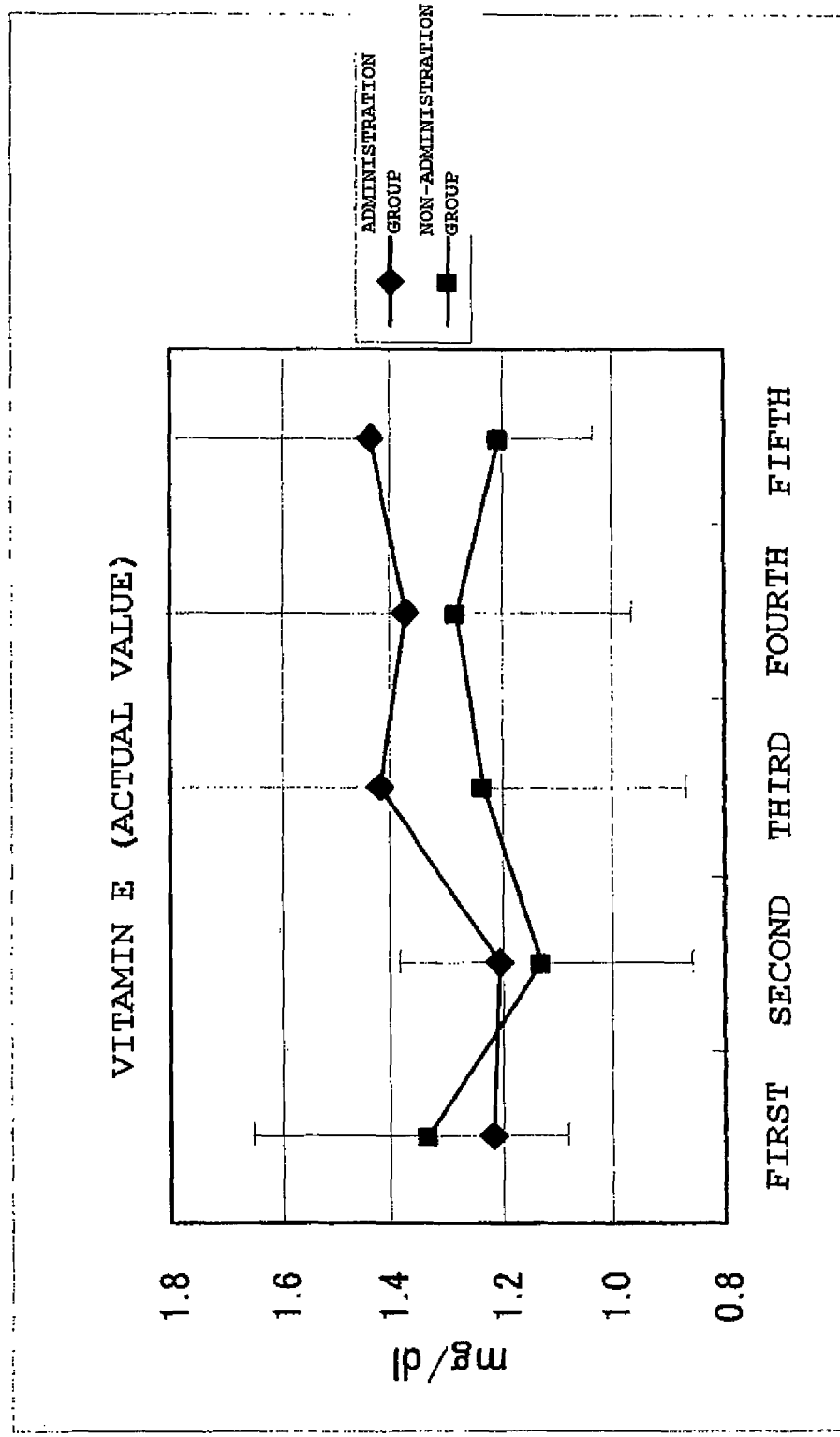
FIG. 8B shows the results of measurement of vitamin E (actual value). A diamond ♦ represents the administration group, and a square ■ represents the non-administration group. Measurement values were averaged out for each group and the values thus obtained were graphed. The vertical axis represents the concentration of vitamin E in the blood (mg/dl) and the horizontal axis represents the respective times of measurement. While a decreasing tendency was exhibited in comparison with the first measurement value in the non-administration group, an increasing tendency was exhibited in the administration group.
Figure 9A:
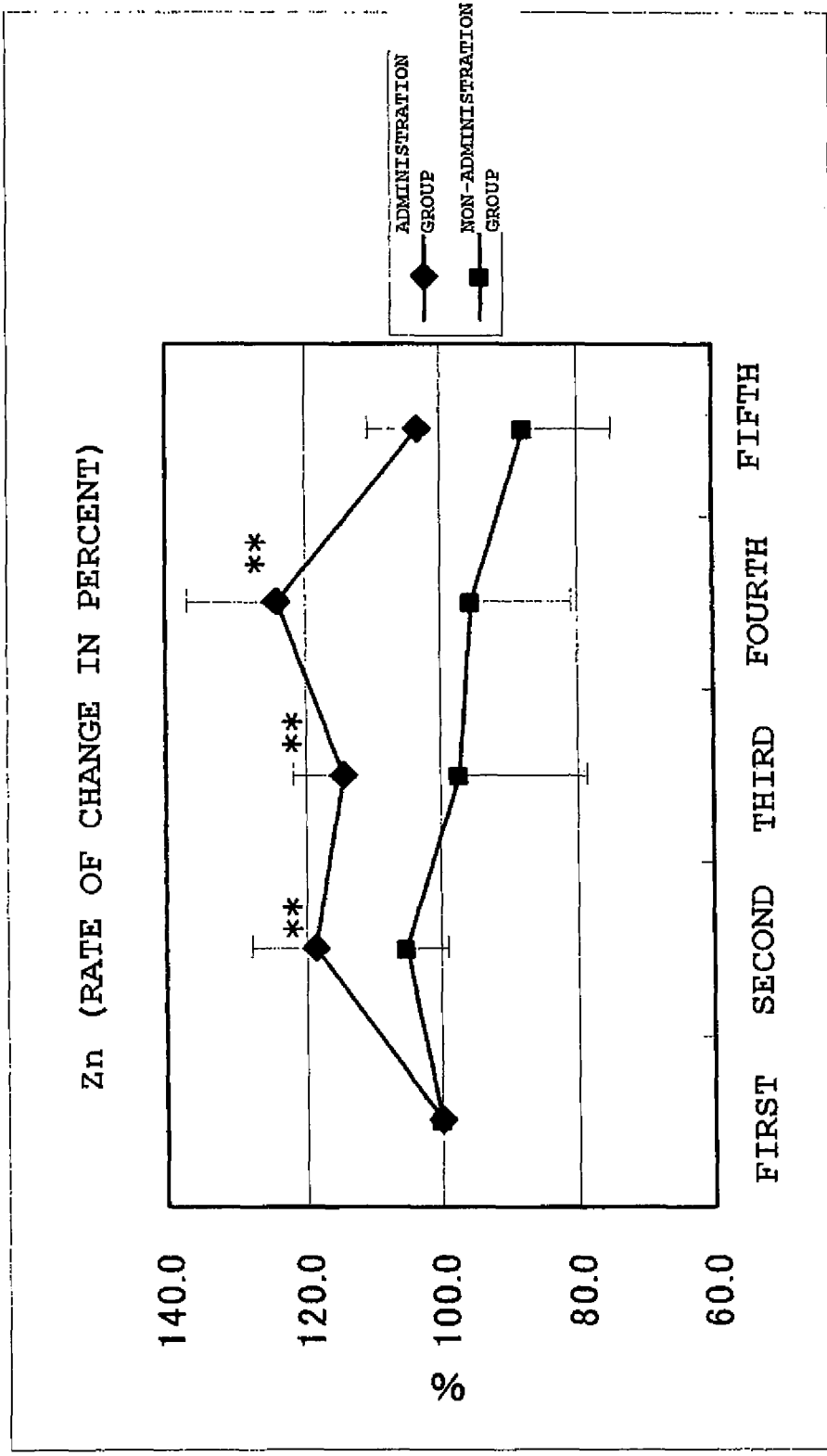
FIG. 9A shows the results of measurement of zinc (rate of change). A diamond ♦ represents the administration group, and a square ■ represents the non-administration group. Rates of change, which were obtained by setting first measurement values at 100%, were averaged out for each group and the values thus obtained were graphed. The vertical axis represents %, and the horizontal axis represents changes over time at each time of measurement. A value for which a significant difference was observed with respect to the first measurement value is indicated by  in each group ( means p<0.01). While the rate of change of zinc was decreased in the non-administration group, it was significantly increased in the administration group.
Figure 9B:
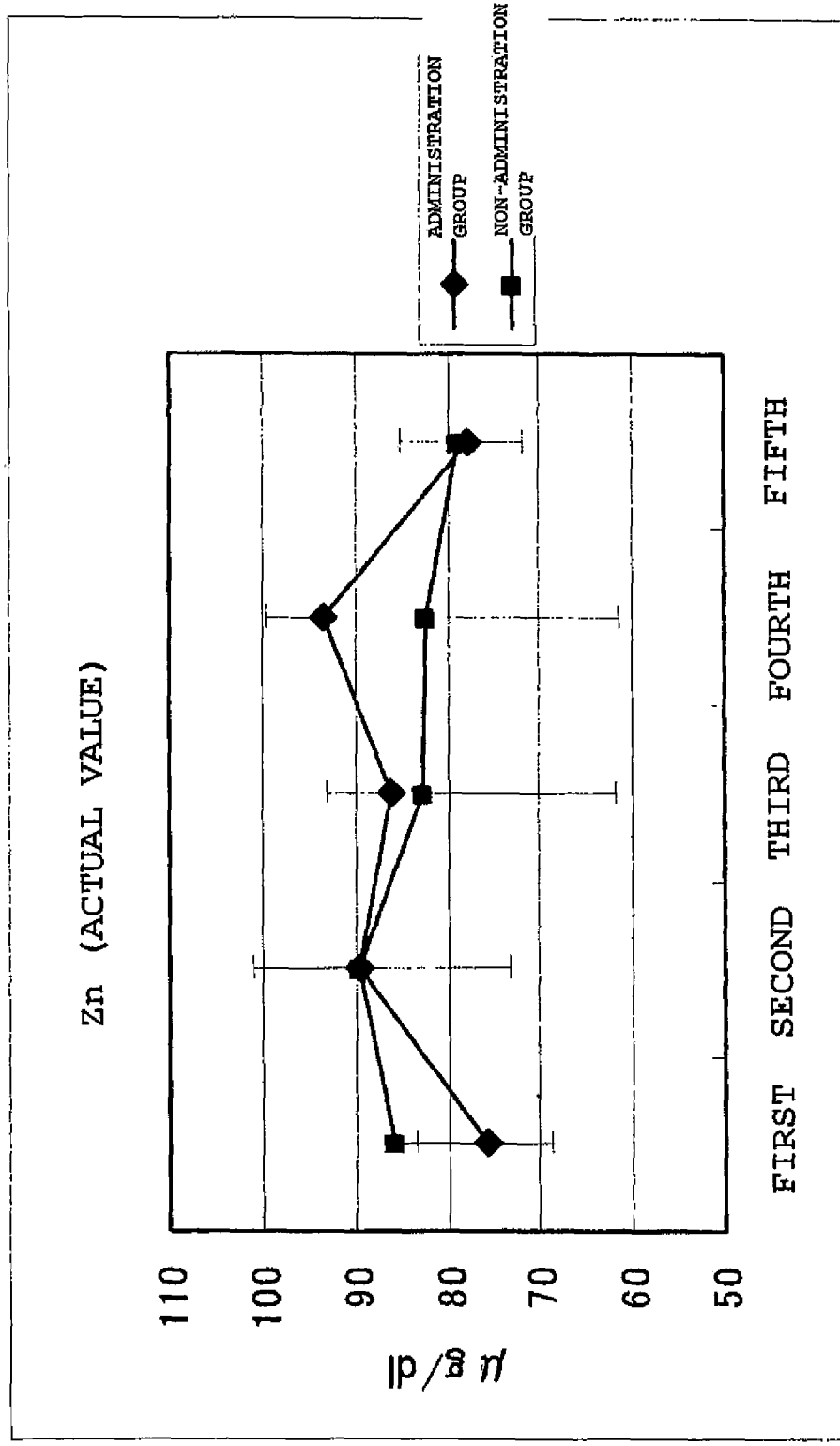
FIG. 9B shows the results of measurement of zinc (actual value). A diamond ♦ represents the administration group, and a square ■ represents the non-administration group. Measurement values were averaged out for each group and the values thus obtained were graphed. The vertical axis represents the concentration of zinc in the blood (µg/dl) and the horizontal axis represents the respective times of measurement. A gradually decreasing tendency was exhibited in the non-administration group. In the administration group, the actual zinc value was decreased at the fifth measurement, but an increasing tendency had been exhibited up until the fourth measurement.
Figure 10A:
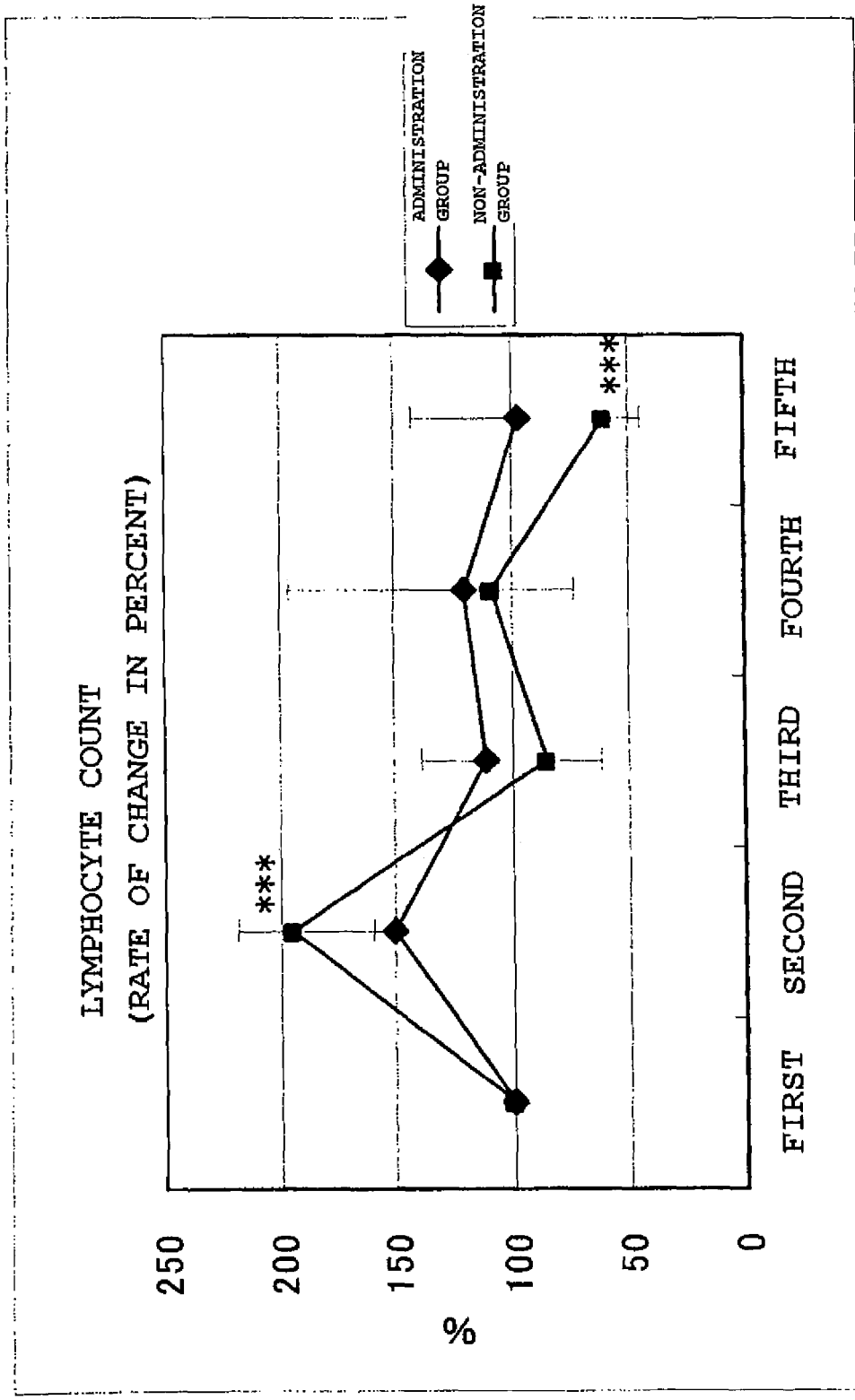
FIG. 10A shows the results of measurement of lymphocyte count (rate of change). A diamond ♦ represents the administration group, and a square ■ represents the non-administration group. Differences from first measurement values were averaged out for each group and the values thus obtained were graphed. A value for which a significant difference was observed in comparison with the first measurement value is indicated by * (* means p<0.001). The vertical axis represents %, and the horizontal axis represents the respective times of measurement. In both of the administration group and the non-administration group, the rates of change in the lymphocyte count were increased at the second measurement but decreasing tendencies were exhibited thereafter.
Figure 10B:
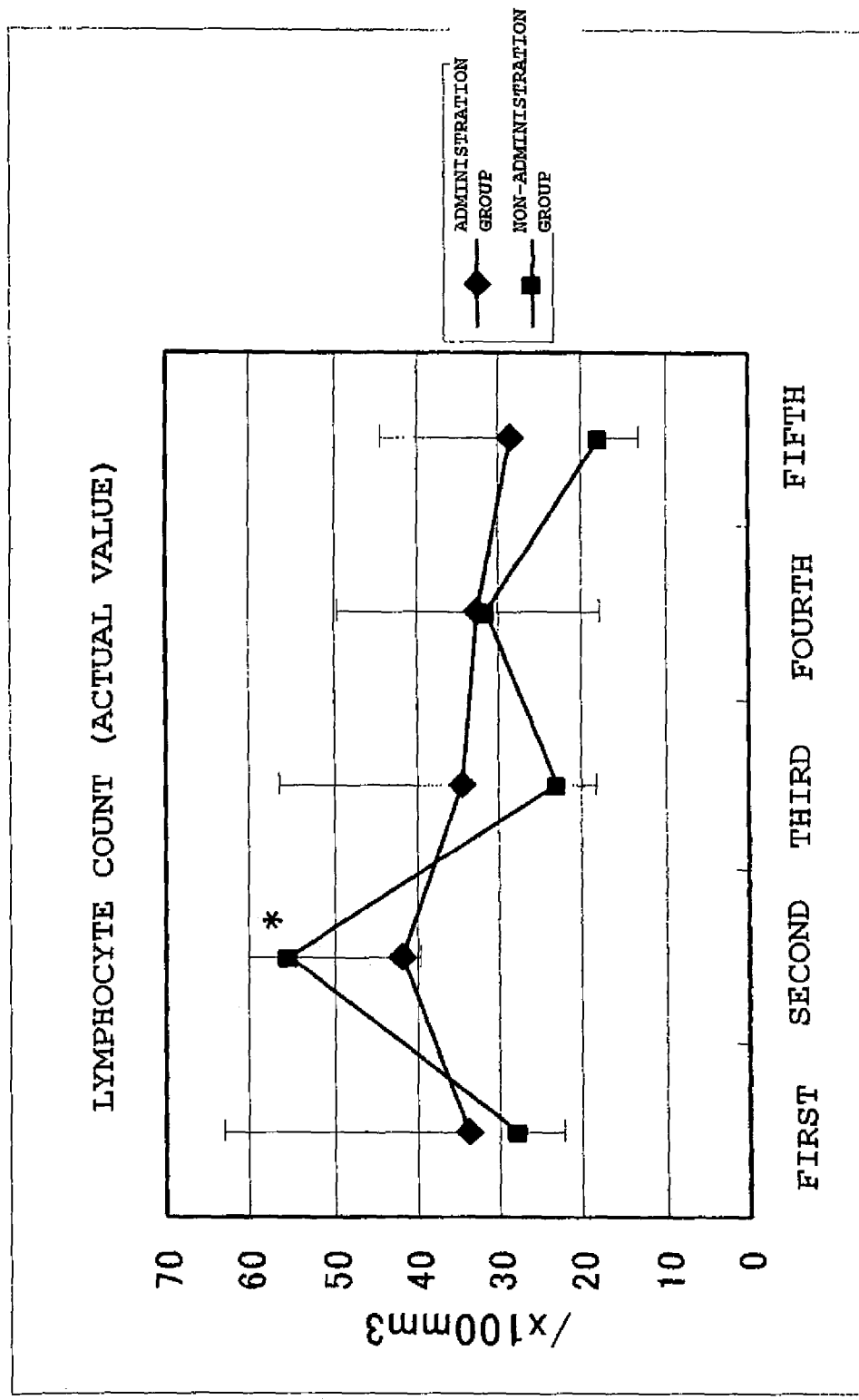
FIG. 10B shows the results of measurement of lymphocyte count (actual value). A diamond ♦ represents the administration group, and a square ■ represents the non-administration group. Measurement values were averaged out for each group and the values thus obtained were graphed. The vertical axis represents the total lymphocyte count (×100 mm3) and the horizontal axis represents the respective times of measurement. In the non-administration group, a significant increase (* p<0.05) was exhibited at the second measurement but the total lymphocyte count was decreased thereafter. In the administration group, a slightly decreasing tendency was exhibited.
Figure 11:
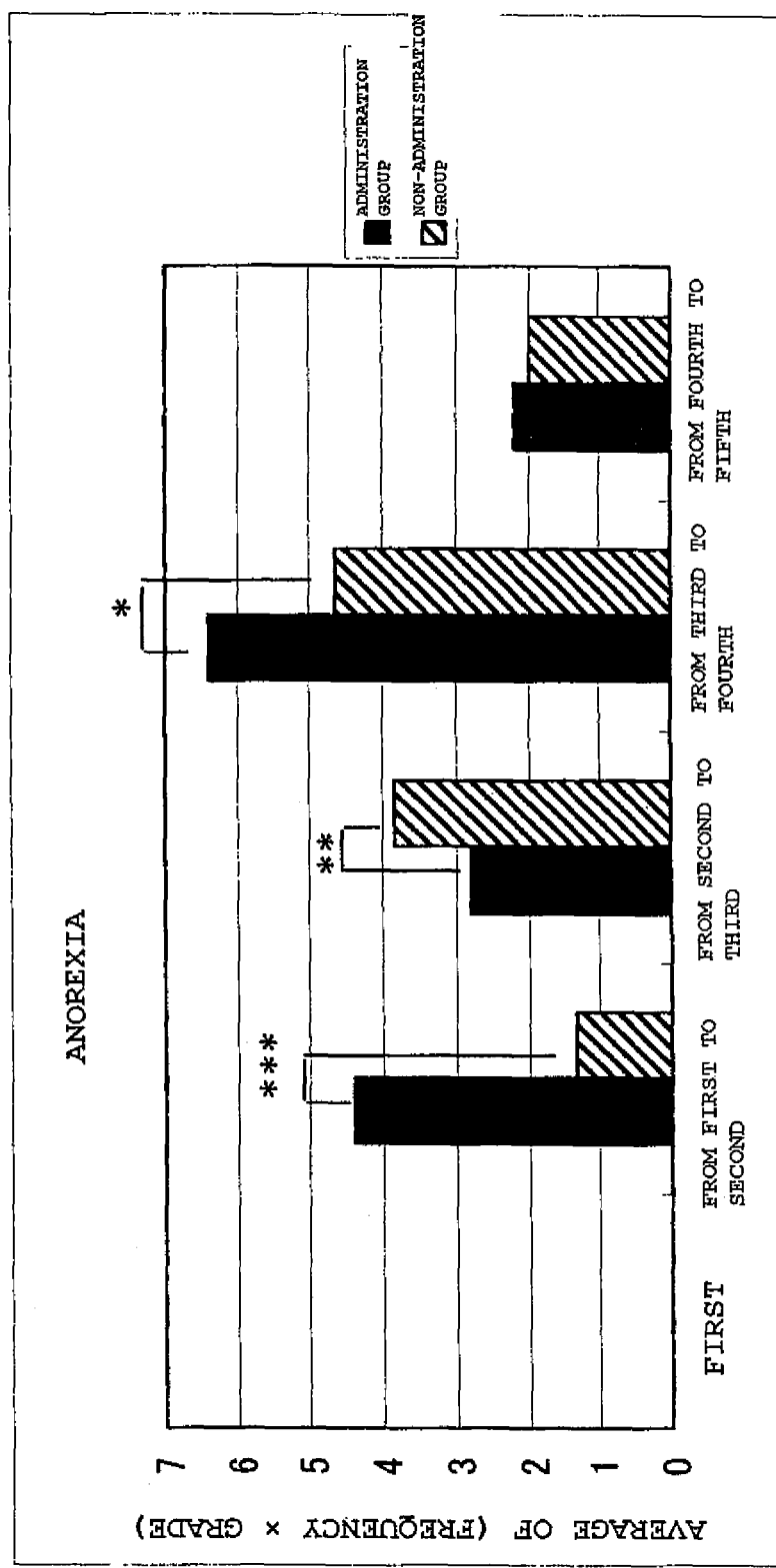
FIG. 11 shows the results for anorexia. A black column represents the administration group, and a hatched column represents the non-administration group. The vertical axis represents an average of the product of the grade and frequency of anorexia, and the horizontal axis represents the period of time between measurements. Anorexia was observed more frequently in the administration group in the periods between the first and second measurements and between the third and fourth measurements, while it was more frequently observed in the non-administration group in the period between the second and third measurements. The symbols *, , and * indicate a significant difference between the two groups (* means p<0.05,  means P<0.01, and * means P<0.001)
Figure 12:
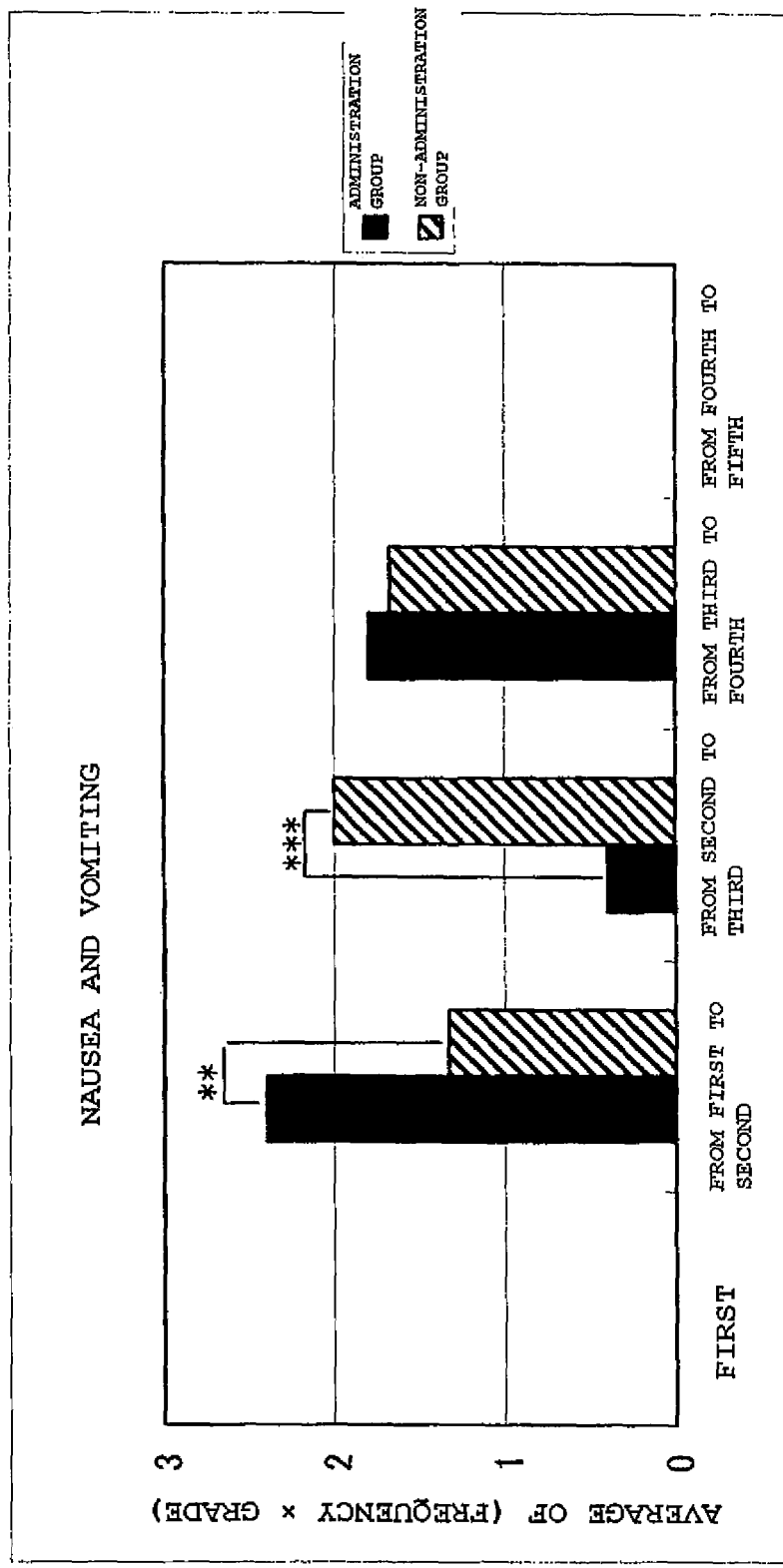
FIG. 12 shows the results for nausea and vomiting. A black column represents the administration group, and a hatched column represents the non-administration group. The vertical axis represents an average of the product of the grade and frequency of nausea and vomiting, and the horizontal axis represents the period of time between measurements. Nausea and vomiting were significantly more frequent in the administration group in the period between the first and second measurements, but in the non-administration group, they were significantly more frequent in the period between the second and third measurements. The symbols  and * indicate a significant difference between the two groups ( means P<0.01 and * means P<0.001)
Figure 13:
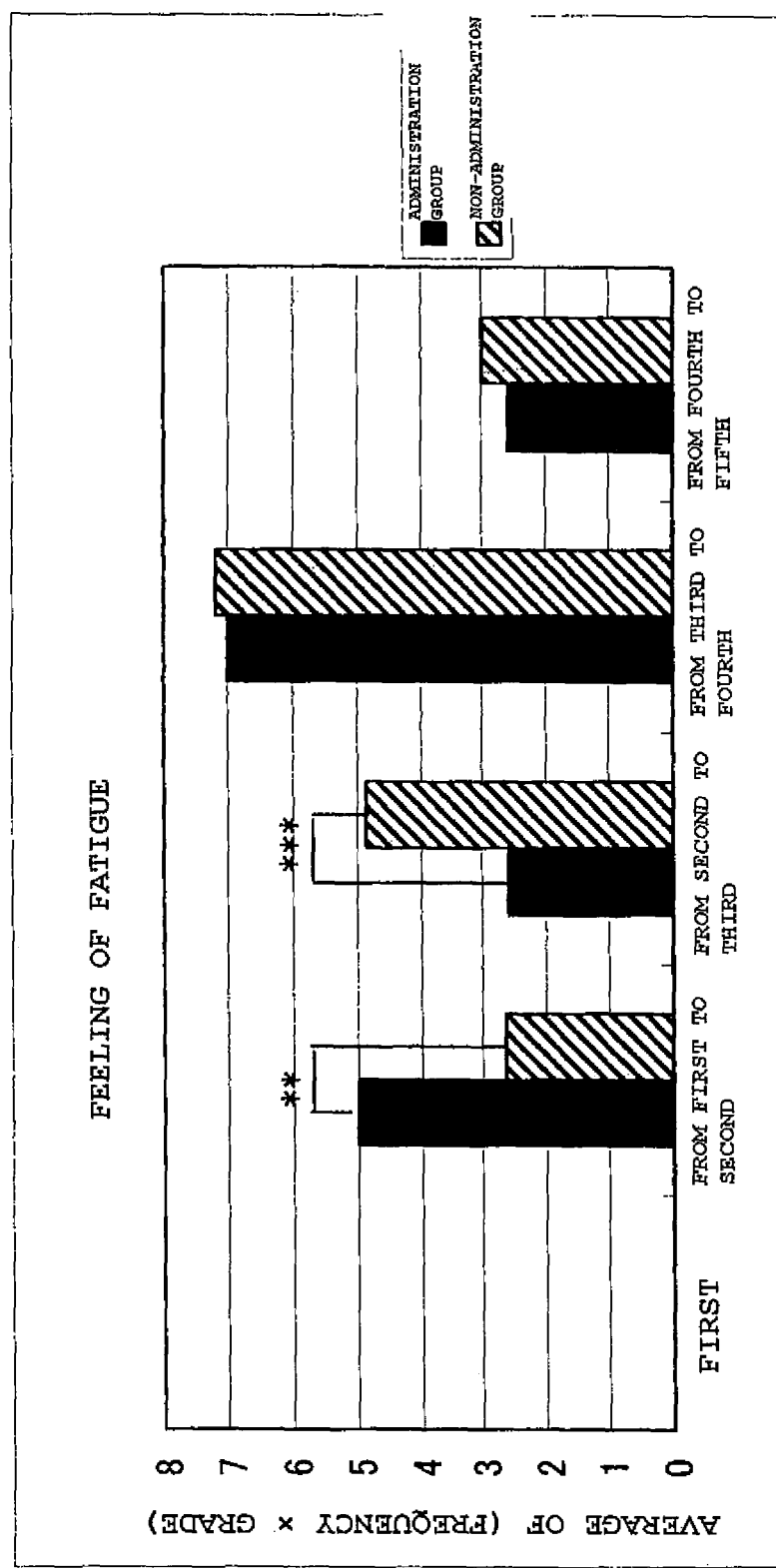
FIG. 13 shows the results for a feeling of fatigue. A black column represents the administration group, and a hatched column represents the non-administration group. The vertical axis represents an average of the product of the grade and frequency of a feeling of fatigue, and the horizontal axis represents the period of time between measurements. While a feeling of fatigue was observed in the administration group in the period between the first and second measurements, it was observed even in the non-administration group in the period between the third and fourth measurements. The symbol * indicates a significant difference between the two groups (* means P<0.001).

The presence or absence of stomatitis, anorexia, nausea, vomiting, feeling of fatigue, and diarrhea, and frequency of development of side effects Results: Results thus obtained are shown in FIGS. 1 to 13.

Albumin, which is an index of a nutritional status, was significantly increased (p<0.01) in the administration group, whereas it was significantly decreased (p<0.001) in the non-administration group, in comparison with the time of initiation of chemotherapy. However, it is to be noted that fluctuation was within the range of the normal values in terms of the actual values. No change was observed with respect to prealbumin in the non-administration group, whereas it was significantly increased (p<0.05) in the administration group. A decreasing tendency was observed with respect to total protein in both groups, while it was significantly decreased (p<0.001) in the non-administration group. Also, an increasing tendency was slightly observed with respect to a radical-generating capacity, which is an index of the amount of active oxygen, in the non-administration group, whereas it was significantly decreased (p<0.01) in the administration group. Although there were decreases at the second and third measurements with respect to lipid peroxide in the administration group, it was increased at the fourth and subsequent measurements, and the value for the fifth measurement was almost the same as that for the first measurement. Vitamin A, vitamin C, vitamin E, and zinc, all having an antioxidant action, were decreased in the non-administration group, whereas they were significantly increased (p<0.01) in the administration group. The lymphocyte count, which is an index of immunity, was found to be slightly increased in the administration group but the change was negligible. In the non-administration group, the lymphocyte count was found to increase by approximately 2000 mm$^3$ at the second measurement but it decreased at the third and subsequent measurements.

With respect to side effects occurring during chemotherapy, each of anorexia, nausea, vomiting, and a feeling of fatigue was significantly decreased (P<0.01) in the administration group, as compared with the non-administration group, in the period between the second and third measurements, during which symptoms of side effects would become particularly severe. From the above, a reducing effect on side effects was observed.

Discussion:

It was considered that the composition of the present invention is particularly effective in improving oxidative stress occurring during cancer chemotherapy and enhancing an antioxidant ability, and also effective in improving a nutritional status.

All the publications, patents and patent applications cited in the present specification are incorporated herein by reference in their entirety.

INDUSTRIAL APPLICABILITY

The composition of the present invention can be used as a trace element-supplemented food and drink for candidate patients for cancer chemotherapy, and is useful for reducing oxidative stress and/or side effects occurring during cancer chemotherapy or improving a nutritional status during cancer chemotherapy.

The invention claimed is:

1. A method for reducing side effects occurring during cancer chemotherapy, comprising
administering orally or through a tube if oral intake is difficult to a subject a composition in amounts effective to reduce the side effects of stomatitis, anorexia, nausea, vomiting, a feeling of fatigue, and diarrhea occurring during cancer chemotherapy, said composition comprising: an antioxidant agent; at least one component selected from the group consisting of vitamin $B_1$, vitamin $B_2$, vitamin $B_6$, niacin, and pantothenic acid; at least one component selected from the group consisting of folic acid, vitamin $B_{12}$, and vitamin A; zinc; selenium; coenzyme Q10; biotin; galacto-oligosaccharide; potassium; calcium; magnesium; and phosphorus,
wherein per dosage unit is provided as follows, 50±10 µg of biotin, 2±0.4 g of galacto-oligosaccharide, 10 to 1000 mg of potassium, 70±14 mg of calcium, 0.1 to 10 mg of magnesium, and 1 to 3500 mg of phosphorus, and
wherein the composition contains no lipids.

2. The method according to claim 1, wherein the antioxidant agent is an antioxidant vitamin.

3. The method according to claim 2, wherein the antioxidant vitamin is at least one member selected from the group consisting of vitamin C, vitamin E, and β-carotene.

4. The method according to claim 1, wherein the components further comprise vitamin $D_3$ and/or iron.

5. The method according to claim 1, wherein the components further comprise vitamin C, vitamin E, β-carotene, vitamin $D_3$, and iron.

6. The method according to claim 5, wherein per dosage unit of the components is as follows, 500±100 mg of vitamin C, 20±4 mg of vitamin E, 6.6±1.32 mg of β-carotene, 3±0.6 mg of vitamin $B_1$, 3±0.6 mg of vitamin $B_2$, 5±1 mg of vitamin $B_6$, 15±3 mg of niacin, 10±2 mg of pantothenic acid, 200 to 1,100 µg of folic acid, 10±2 µg of vitamin $B_{12}$, 500±110 µg of vitamin A (retinol equivalent), 10±2 mg of zinc, 50±10 µg of selenium, 15±3 mg of coenzyme Q10, 3.7±0.74 µg or 5±1 of vitamin $D_3$, and 5±1 mg of iron, and having an energy of 80±16 kcal.

7. The method according to claim 1, wherein the components are administered in a liquid that can be taken.

8. The method according to claim 7, wherein the liquid is fruit juice.

9. The method according to claim 7, having a volume of 125±25 mL per dosage unit.

10. The method according to claim 1, wherein the subject has hematologic neoplasm.

11. A method for reducing side effects occurring during cancer chemotherapy, comprising
administering orally or through a tube if oral intake is difficult to a subject a composition in amounts effective to reduce the side effects of stomatitis, anorexia, nausea, vomiting, a feeling of fatigue, and diarrhea occurring during cancer chemotherapy, the composition comprising: an antioxidant agent; at least one component selected from the group consisting of vitamin $B_1$, vitamin $B_2$, vitamin $B_6$, niacin, and pantothenic acid; at least one component selected from the group consisting of folic acid, vitamin $B_{12}$, and vitamin A; zinc; selenium; coenzyme Q10; biotin; galacto-oligosaccharide; potassium; calcium; magnesium; and phosphorus,
wherein the composition contains no lipids, and
conducting on the subject one or more of biochemical examinations selected from the group consisting of: erythrocyte count, leukocyte count, leukocyte fraction, lymphocyte count, total protein, albumin, blood glucose level, total cholesterol, triglyceride, CRP, Hb, prealbumin, radical-generating capacity, lipid peroxide, and Zn.

12. A method for reducing side effects occurring during cancer chemotherapy, comprising:
administering orally or through a tube if oral intake is difficult to a subject a composition in amounts effective to reduce the side effects of stomatitis, anorexia, nausea, vomiting, a feeling of fatigue, and diarrhea occurring during cancer chemotherapy, the composition comprising: 500±100 mg of vitamin C, 20±4 mg of vitamin E, 3±0.6 mg of vitamin $B_1$, 3±0.6 mg of vitamin $B_2$, 5±1 mg of vitamin $B_6$, 15±3 mg of niacin, 10±2 mg of pantothenic acid, 200±110 µg of folic acid, 10±2 µg of vitamin $B_{12}$, 300±60 µg of vitamin A (retinol equivalent), 10±2 mg of zinc, 50±10 µg of selenium, 30±6 µg of chromium, 5±1 µg of vitamin $D_3$, 50±10 µg of biotin, 2±0.4 g of galacto-oligosaccharide, 40±8 mg of potassium, 80±16 mg of calcium, 3±0.6 mg of magnesium, and 7.5±1.5 mg of phosphorus, and 30±6 mg of α-lipoic acid, wherein the composition contains no lipids, and conducting on the subject one or more of biochemical examinations selected from the group consisting of: erythrocyte count, leukocyte count, leukocyte fraction, lymphocyte count, total protein, albumin, blood glucose level, total cholesterol, triglyceride, CRP, Hb, prealbumin, radical-generating capacity, lipid peroxide, and Zn.

13. A method for reducing side effects occurring during cancer chemotherapy according to claim 11, wherein results of one or more of the biochemical examinations are compared correspondingly against the following ranges: 4.4 million to 5.4 million erythrocytes/mm3 (male) and 3.8 million to 4.6 million erythrocytes/mm3 (female); 4000 to 8000 leukocytes/μl; a leukocyte fraction containing 3 to 6% of stab neutrophils, 45 to 55% of segmented neutrophils, 1 to 5% of eosinophils, 0 to 1% of basophils, 25 to 45% of lymphocytes, and 4 to 7% of monocytes; 1500 to 3000 total lymphocytes mm3; 6.5 to 8.2 g total protein/dl; 3.5 to 5.0 g albumin/dl; a fasting blood glucose level of 70 to 110 mg/dl; 120 to 220 mg total cholesterol/dl; 40 to 150 mg triglyceride/dl; 0 to 0.2 mg CRP/dl; 14 to 18 g Hb/dl; 10 to 40 mg prealbumin/dl; a radical-generating capacity of 0.0 to 1.3 nmol/ml; lipid peroxide; and 70 to 140 μg Zn/dl.

14. A method for reducing side effects occurring during cancer chemotherapy according to claim 12, wherein results of one or more of the biochemical examinations are compared correspondingly against the following ranges: 4.4 million to 5.4 million erythrocytes/mm3 (male) and 3.8 million to 4.6 million erythrocytes/mm3 (female); 4000 to 8000 leukocytes/μl; a leukocyte fraction containing 3 to 6% of stab neutrophils, 45 to 55% of segmented neutrophils, 1 to 5% of eosinophils, 0 to 1% of basophils, 25 to 45% of lymphocytes, and 4 to 7% of monocytes; 1500 to 3000 total lymphocytes mm3; 6.5 to 8.2 g total protein/dl; 3.5 to 5.0 g albumin/dl; a fasting blood glucose level of 70 to 110 mg/dl; 120 to 220 mg total cholesterol/dl; 40 to 150 mg triglyceride/dl; 0 to 0.2 mg CRP/dl; 14 to 18 g Hb/dl; 10 to 40 mg prealbumin/dl; a radical-generating capacity of 0.0 to 1.3 nmol/ml; lipid peroxide; and 70 to 140 μg Zn/dl.

* * * * *